(12) United States Patent
Sitek

(10) Patent No.: US 10,827,982 B2
(45) Date of Patent: Nov. 10, 2020

(54) CONVOLUTIONAL DEEP LEARNING ANALYSIS OF TEMPORAL CARDIAC IMAGES

(71) Applicant: KONINKLIJKE PHILIPS N.V., Eindhoven (NL)

(72) Inventor: Arkadiusz Sitek, Ashland, MA (US)

(73) Assignee: Koninklijke Philips N.V., Eindhoven (NL)

( * ) Notice: Subject to any disclaimer, the term of this patent is extended or adjusted under 35 U.S.C. 154(b) by 353 days.

(21) Appl. No.: 15/978,981

(22) Filed: May 14, 2018

(65) Prior Publication Data

US 2018/0333104 A1 Nov. 22, 2018

Related U.S. Application Data

(60) Provisional application No. 62/508,087, filed on May 18, 2017.

(51) Int. Cl.
| | |
|---|---|
| A61B 5/00 | (2006.01) |
| G06N 5/04 | (2006.01) |
| A61B 5/0468 | (2006.01) |
| G06T 7/00 | (2017.01) |
| G06N 3/08 | (2006.01) |
| G06N 3/04 | (2006.01) |

(52) U.S. Cl.
CPC .......... *A61B 5/7267* (2013.01); *A61B 5/0468* (2013.01); *G06N 3/0454* (2013.01); *G06N 3/08* (2013.01); *G06N 5/046* (2013.01); *G06T 7/0012* (2013.01); *G06N 3/0445* (2013.01); *G06T 2207/10081* (2013.01); *G06T 2207/10088* (2013.01); *G06T 2207/10104* (2013.01); *G06T 2207/10108* (2013.01); *G06T 2207/10121* (2013.01); *G06T 2207/10132* (2013.01); *G06T 2207/30048* (2013.01)

(58) Field of Classification Search
CPC ........................... A61B 5/7267; A61B 5/0469
See application file for complete search history.

(56) References Cited

PUBLICATIONS

Narula, S. et al., "Machine-learning algorithms to automate morphological and functional assessments in 2D echocardiology", Journal of the American College of Cardiology, 2016.
(Continued)

*Primary Examiner* — Joseph M Santos Rodriguez

(57) ABSTRACT

A convolutional neural cardiac diagnostic system employs an echocardiogram diagnostic controller for controlling a diagnosis of an echocardiogram including a temporal sequence of echocardiac cycles. The echocardiogram diagnostic controller includes a diagnostic periodic volume generator generating an echocardiogram diagnostic volume including a periodic stacking of the temporal sequence of echocardiac cycles, and further includes a diagnostic convolutional neural network classifying the echocardiogram as either a normal echocardiogram or an abnormal echocardiogram based on a convolutional neural analysis of the echocardiogram diagnostic volume. The diagnostic periodic volume generator may further generate an electrocardiogram diagnostic volume including a periodic stacking of the temporal sequence of electrocardiac waves, and the convolutional neural network may classify the echocardiogram as either a normal echocardiogram or an abnormal echocardiogram based on a convolutional neural analysis of both the echocardiogram diagnostic volume and the electrocardiogram diagnostic volume.

20 Claims, 20 Drawing Sheets

(56) References Cited

PUBLICATIONS

Huang, W. et al., "Temporal HeartNet: Towards Human-Level Automatic Analysis of Fetal Cardiac Screening Video", Department of Engineering Science, University of Oxford, 2017.

Slomka, P. et al., "Cardiac imaging: working towards fully-automated machine analysis and interpretation", Expert Review of Medical Devices, 2017.

Simonyan, et al., "Two-Stream Convolutional Networks for Action Recognition in Videos", Visual Geometry Group, University of Oxford, Nov. 12, 2014, pp. 1-11.

Karpathy, et al., "Large-scale Video Classification with Convolutional Neural Networks", Computer Science Department, Stanford University, http://cs.stanford.edu/people/karpathy/deepvideo, 8 pages.

Donahue, et al., "Long-term Recurrent Convolutional Networks for Visual Recognition and Description", Feb. 17, 2015, pp. 1-13.

Simonite, T., "IBM's Automated Radiologist Can Read Images and Medical Records", https://www.technologyreview.com/s/600706/ibmsautomatedradiologistcanreadimagesandmedicalrecords/; Feb. 4, 2016, 4 pages.

Berlage, et al., "Supporting Ultrasound Diagnosis Using an Animated 3D Model of the Heart", Proceedings of IEEE Multimedia Computing and Systems (Hiroshima, Japan, Jun. 17-21, 1996, pp. 1-6.

Cannesson, et al., "A Novel Two-Dimensional Echocardiographic Image Analysis System Using Artificial Intelligence-Learned Pattern Recognition for Rapid Automated Ejection Fraction", Journal of the American College of Cardiology, vol. 49, No. 2, Jan. 16, 2007, pp. 217-226.

Gao, et al., "A fused deep learning architecture for viewpoint classification of echocardiography", Information Fusion, vol. 36, Jul. 2017, 3 pages (Abstract).

Margeta, J., "Machine Learning for Simplifying th Use of Cardiac Image Databases", https://pastel.archives-ouvertes.fr/tel-01243340v2, submitted on Apr. 25, 2016, 194 pages.

CONVOLUTIONAL DEEP LEARNING ANALYSIS OF TEMPORAL CARDIAC IMAGES

CROSS REFERENCE TO RELATED APPLICATION

The present application claims the benefit of U.S. Provisional Application No. 62/508,087, filed May 18, 2017. These applications are hereby icorporated by reference herein.

TECHNICAL FIELD

The present disclosure generally relates to image processing. More specifically, but not exclusively, the present disclosure relates to classifying a cardiac image as illustrating normal cardiac functions or abnormal cardiac functions.

BACKGROUND

Many medical imaging modalities (e.g., ultrasound US, magnetic resonance imaging MRI, CT, positron emission tomography PET, etc.) provide temporal data describing functions of various body organs. One of the main application of the temporal functional imaging is the diagnosis and monitoring of heart disease. Because the heart is in constant periodic motion, the temporal imaging is extensively used to characterize cardiac function by analysis of the cardiac deformation.

Echocardiography (echo) as known in the art of the present disclosure is one of the most popular techniques used to capture the temporal data of a beating heart. Echo has several advantages over other imaging modalities that include low cost and portability. Echo real-time imaging and does not use any ionizing radiation.

There are two (2) different acquisition modes, the most widely utilized two-dimensional (2D) mode and a less popular three-dimensional mode (3D) mode.

For 2D echo, an ultrasound transducer is positioned close to the sternum and images in 2D planes intersecting the heart are acquired at 50 to 100 per second frame rate. These movies (temporal sequence of planar echocardiac images) are visualized live for the sonographer and can be saved and sent for later interpretation/diagnosis (e.g. PACS). 2D echo requires an acquisition of several different planes going through the heart to cover the entire volume of the myocardium.

For 3D echo, a more sophisticated transducer is used and temporal sequence of volumetric echocardiac images of beating heart are acquired.

An electrocardiogram (ECG) as known in the art of the present disclosure increases an ability to detect abnormal cardiovascular conditions (e.g., cardiomyopathies) that may lead to sudden cardiac arrest. The result of the ECG is a waveform that indicates the electrical activity of the heart during the heart cycle, and an ECG is simultaneously performed with an echo to enhance the cardiac diagnosis.

One major application of Echo is the detection and characterization of cardiovascular disease (CVD). The disease may be a result of occlusion in one or more coronary arteries which results in reduced contractility of one or more of the segments of the heart. In clinical applications of echo, the abnormalities in cardiac wall motion are detected based on temporal echo images and quantified. In the current practice, this quantification is done by subjective visual examination of the temporal images and detection of cardiac wall motion and thickening abnormalities per myocardial segment. The interpretation of the Echo may be done either during the examination as the images are visualized real-time or post examination at the reading console (e.g. PACS). There are many other types of cardiac diseases that come from abnormalities in cardiac function either electrical or mechanical in nature. The common dominator of those diseases if that they manifest in either the cardiac structure or/and in function (electrical/mechanical).

There is a substantial research effort done into modelling of cardiac deformation as evidenced by echo images. Majority of those efforts are based on image analysis. For example, detection of endocardial wall may be utilized and then quantified. Also, segmentation, speckle tracking, non-rigid registration approaches may be utilized to automatically track the cardiac motion and determine the motion abnormalities. However, all of those approaches suffer from a problem of severe noise in ultrasound images which prevents the robust implementation of these algorithms.

A different approach to this problem is to use a different data acquisition model involving a Doppler acquisition of ultrasound in which motion of tissues can be quantified. For this approach however, the motion can only be quantified in beam direction and results are dependent on the signal-to-noise ratio.

SUMMARY

One of the major problems of the aforementioned Echo procedures is the diagnosis of CVD based on motion of the cardiac wall is done in a completely subjective manner. An echocardiographer eyeballs the temporal views and based on those views determines which segments exhibit motion abnormalities indicative of a reduced cardiac fiber contractility due to CVD.

The visual assessment that is used today is highly dependent on experience and training of an echocardiographer. It follows that inter-observer and intra-observer variability is significant. The other difficulty with interpretation of Echo is that it requires highly trained professionals needed for interpretation of echo images. If they are not promptly available or not available all the utility of Echo is substantially reduced for instant diagnosis.

Moreover, as previously stated, echo examinations are typically accompanied by the acquisition of ECG waveforms. However, the echo and the ECG are interpreted separately reducing the synergy of these tests.

To improve upon detection and characterization of cardiovascular disease (CVD) via acquisition of echo cardiac images, the present disclosure provides systems, devices, controllers and methods for standardizing a classification/ quantification of abnormal cardiac conditions (e.g., heart wall motion abnormalities) evidenced by echo cardiac images which may be combined with electrocardiograms to thereby standardize a diagnosis of CVD using echo.

Generally, the present disclosure is premised on application of a deep convolutional neural network to an echocardiogram based on a modelling of temporal changes in the echocardiogram.

One embodiment of the present disclosure is a convolutional neural cardiac diagnostic system including one or more of the following: an ultrasound device for generating echocardiogram data and an echocardiogram controller for controlling a generation of an echocardiogram derived from the echocardiogram data. The echocardiogram includes a temporal sequence of echocardiac cycles.

The convolutional neural cardiac diagnostic system further includes a cardiac diagnostic controller for controlling a diagnosis of the echocardiogram. To this end, the cardiac diagnostic controller includes a periodic volume generator for generating an echocardiogram diagnostic volume including a periodic stacking of the temporal sequence of echocardiac cycles and further includes a diagnostic convolutional neural network for classifying(quantifying) the echocardiogram as one of a normal echocardiogram or an abnormal echocardiogram based on a convolutional neural analysis of the echocardiogram diagnostic volume.

A second embodiment of the present disclosure is the convolutional neural diagnostic echo system further including a lead system for generating electrocardiogram data, and an electrocardiogram controller for controlling a generation of an electrocardiogram derived from the electrocardiogram data. The electrocardiogram includes a temporal sequence of electrocardiogram waves.

The periodic volume generator further generates an electrocardiogram diagnostic volume including a periodic stacking of the temporal sequence of electrocardiogram waves, and the diagnostic convolutional neural network classifies (quantifies) the echocardiogram as one of the normal echocardiogram or the abnormal echocardiogram based on a convolutional neural analysis of both the echocardiogram diagnostic volume and the electrocardiogram diagnostic volume.

A third embodiment of the present disclosure is a convolutional neural cardiac diagnostic method including one or more of the following an ultrasound device generating echocardiogram data, and an echocardiogram controller controlling a generation of an echocardiogram derived from the echocardiogram data. The echocardiogram includes a temporal sequence of echocardiac cycles.

The convolutional neural cardiac diagnostic method further includes a cardiac diagnostic controller controlling a diagnosis of the echocardiogram by generating an echocardiogram diagnostic volume including a periodic stacking of the temporal sequence of echocardiac cycles, and further by classifying(quantifying) the echocardiogram as one of a normal echocardiogram or an abnormal echocardiogram based on a convolutional neural analysis of the echocardiogram diagnostic volume.

A fourth embodiment of the present disclosure is the convolutional neural diagnostic echo method including a lead system generating electrocardiogram data, and an electrocardiogram controller controlling a generation of an electrocardiogram derived from electrocardiogram data. The electrocardiogram includes a temporal sequence of electrocardiogram waves.

The convolutional neural cardiac diagnostic method further includes the cardiac diagnostic controller controlling the diagnosis of the echocardiogram by generating an electrocardiogram diagnostic volume including a periodic stacking of the temporal sequence of electrocardiac waves and by further classifying(quantifying) the echocardiogram as one of a normal echocardiogram or an abnormal echocardiogram based on a convolutional neural analysis of both the echocardiogram diagnostic volume and the electrocardiogram diagnostic volume.

Various embodiments described herein relate to a convolutional neural cardiac diagnostic system, including one or more of the following: an ultrasound device structurally configured to generate echocardiogram data; an echocardiogram controller structurally configured to control a generation of an echocardiogram derived from a generation of the echocardiogram data by the ultrasound device, the echocardiogram including a temporal sequence of echocardiac cycles; and an echocardiogram diagnostic controller structurally configured to control a diagnosis of the echocardiogram, wherein the echocardiogram diagnostic controller includes: a diagnostic periodic volume generator structurally configured to generate an echocardiogram diagnostic volume derived from a generation of the echocardiogram by the echocardiogram controller, the echocardiogram diagnostic volume including a periodic stacking of the temporal sequence of echocardiac cycles; and a diagnostic convolutional neural network structurally configured to classify the echocardiogram as one of a normal echocardiogram or an abnormal echocardiogram based on a convolutional neural analysis of the echocardiogram diagnostic volume as generated by the diagnostic periodic volume generator.

Various embodiments described herein relate to a convolutional neural cardiac diagnostic system, including one or more of the following: a medical imaging modality structurally configured to generate cardiac imaging data; a cardiogram controller structurally configured to control a generation of a cardiogram derived from a generation of the cardiac imaging data by the imaging modality, the cardiogram including a temporal sequence of cardiac cycles; and a cardiogram diagnostic controller structurally configured to control a diagnosis of the a cardiogram, wherein the cardiogram diagnostic controller includes: a diagnostic periodic volume generator structurally configured to generate a cardiogram diagnostic volume derived from a generation of the cardiogram by the cardiogram controller, the cardiogram diagnostic volume including a periodic stacking of the temporal sequence of cardiac cycles; and a diagnostic convolutional neural network structurally configured to classify the cardiogram as one of a normal cardiogram or an abnormal cardiogram based on a convolutional neural analysis of the cardiogram diagnostic volume as generated by the diagnostic periodic volume generator.

Various embodiments described herein relate to a convolutional neural cardiac diagnostic method, one or more of the following: an ultrasound device generating echocardiogram data; an echocardiogram controller controlling a generation of an echocardiogram derived from the generation of the echocardiogram data by the ultrasound device, the echocardiogram including a temporal sequence of echocardiac cycles; and an echocardiogram diagnostic controller controlling a diagnosis of the echocardiogram including: the echocardiogram diagnostic controller generating an echocardiogram diagnostic volume derived from a generation of the echocardiogram by the echocardiogram controller, the echocardiogram diagnostic volume including a periodic stacking of the temporal sequence of echocardiac cycles; and the echocardiogram diagnostic controller classifying the echocardiogram as one of a normal echocardiogram or an abnormal echocardiogram based on a convolutional neural analysis of the echocardiogram diagnostic volume.

Various embodiments described herein relate to a non-transitory machine-readable storage medium (e.g., a volatile or non-volatile memory) including instructions for execution by a processor, the medium including one or more of: instructions for generating echocardiogram data; instructions for controlling a generation of an echocardiogram derived from the generation of the echocardiogram data by the ultrasound device, the echocardiogram data including a temporal sequence of echocardiac cycles; and instructions for controlling a diagnosis of the echocardiogram including: instructions for generating an echocardiogram diagnostic volume derived from a generation of the echocardiogram by the echocardiogram controller, the echocardiogram diagnostic volume including a periodic stacking of the temporal sequence of echocardiac cycles; and instructions for classifying the echocardiogram as one of a normal echocardiogram or an abnormal echocardiogram based on a convolutional neural analysis of the echocardiogram diagnostic volume.

Various embodiments are described wherein the temporal sequence of echocardiac cycles include one of: planar echocardiac images; and volumetric echocardiac images Various embodiments are described wherein the echocardiogram includes an additional temporal sequence of echocardiac cycles; wherein the diagnostic periodic volume generator is further structurally configured to generate an additional echocardiogram diagnostic volume including an periodic stacking of the additional temporal sequence of echocardiac cycles; and wherein the diagnostic convolutional neural network is further structurally configured to classify the echocardiogram as one of a normal echocardiogram or an abnormal echocardiogram based on a convolutional neural analysis of both the echocardiogram diagnostic volume and the additional echocardiogram diagnostic volume as generated by the diagnostic periodic volume generator.

Various embodiments are described wherein the diagnostic convolutional neural network includes a spatial-temporal based convolutional neural network.

Various embodiments are described wherein the diagnostic convolutional neural network includes a memory recurrent network based convolutional neural network.

Various embodiments are described wherein the diagnostic convolutional neural network includes a multiple stream based convolutional neural network.

Various embodiments additionally include a lead system structurally configured to generate electrocardiogram data; an electrocardiogram controller structurally configured to control a generation of an electrocardiogram derived from a generation of the electrocardiogram data by the lead system, the electrocardiogram including a temporal sequence of electrocardiac wave s; wherein the diagnostic periodic volume generator is further structurally configured to generate an electrocardiogram diagnostic volume derived from a generation of the electrocardiogram by the electrocardiogram controller, the electrocardiogram diagnostic volume including a periodic stacking of the temporal sequence of electrocardiac wave s; and wherein the diagnostic convolutional neural network is structurally configured to classify the echocardiogram as one of the normal echocardiogram or the abnormal echocardiogram based on a convolutional neural analysis of both the echocardiogram diagnostic volume and the electrocardiogram diagnostic volume as generated by the diagnostic periodic volume generator.

For purposes of describing and claiming the various embodiments of the present disclosure, (1) terms of the art including, but not limited to, "cardiogram" "echocardiogram", "electrocardiogram", "convolutional neural network", "classifying", "quantifying (synonymous with classifying)", and "medical imaging modality" are to be interpreted as understood in the art of the present disclosure and as exemplary described in the present disclosure;

(2) the term "normal" as a descriptive labeling of any type of cardiogram in the present disclosure broadly encompasses, as would be understood by those of ordinary of skill in the art of the present disclosure and as exemplary described in the present disclosure, a cardiogram exhibiting well known characteristics of a heart representative of an absence of any type of unhealthy/fatal cardiovascular condition. Examples of a normal cardiogram include, but are not limited to, an echocardiogram exhibiting normal cardiac wall motion related to any structural or functional abnormality and an electrocardiogram exhibiting normal electrical activity;

(3) the term "abnormal" as descriptive of any type of cardiogram in the present disclosure broadly encompasses, as would be understood by those of ordinary of skill in the art of the present disclosure and as exemplary described in the present disclosure, a cardiogram exhibiting well known characteristics of a heart representative of an absence of any type of unhealthy/fatal cardiovascular condition. Examples of an abnormal cardiogram include, but are not limited to, an echocardiogram exhibiting abnormal cardiac wall motion related to any structural or functional abnormality and an electrocardiogram exhibiting abnormal electrical activity;

(4) the term "echocardiac cycle" broadly encompasses, as would be understood by those of ordinary of skill in the art of the present disclosure and as exemplary described in the present disclosure, a temporal sequence of 2D echocardiac images over a single heartbeat, or a temporal sequence of 3D echocardiac images over a single heartbeat;

(5) the term "electrocardiac wave" broadly encompasses, as would understood by those ordinary of skill in the art of the present disclosure and as exemplary described in the present disclosure, an electrocardiogram waveform over a single heartbeat;

(6) the term "convolutional neural analysis" broadly encompasses, as understood in the art of the present disclosure and as exemplary described in the present disclosure, a classification of one or more image volumes based of a connection of features within the image volume(s). Examples of a convolutional neural analysis include, but is not limited to, a spatial-temporal convolutional neural analysis, a multiple stream convolutional neural analysis and a memory recurrent convolutional neural analysis;

(7) the term "periodic stacking" broadly encompasses, as exemplary described in the present disclosure, an image digital stacking of a temporal sequence of echocardiac cycles whereby a last echocardiac slice of any given echocardiac cycle is a neighbor of a first echo echocardiac slice of any succeeding echocardiac cycle or an image digital stacking of a temporal sequence of electrocardiac waves;

(8) the term "convolutional neural cardiac diagnostic system" broadly encompasses all cardiac diagnostic systems, as known in the art of the present disclosure and hereinafter conceived, incorporating the principles of the present disclosure for implementing a deep convolutional neural network to an echocardiogram based on a modelling of temporal changes in the echocardiogram. Examples of known cardiac diagnostic systems include, but are not limited to, point-of-care ultrasound ultralight scanners— hand held devices (e.g., Philips Lumify and GE Vscan, portable ultrasound systems (e.g., Philips CX50 POC, Philips Sparq, GE Logiq series and GE Vivid cardiovascular series), cardiology solutions scanners (e.g., Philips EPIC 7, EPIC 5) and interventional cardiology (e.g., Philips CX50 xMATRIX);

(9) the term "convolutional neural cardiac diagnostic method" broadly encompasses all convolutional neural cardiac diagnostic methods, as known in the art of the present disclosure and hereinafter conceived, incorporating the principles of the present disclosure implementing a deep convolutional neural network to an echocardiogram based on a modelling of temporal changes in the echocardiogram. A non-limiting example of a known surface scanning method is Philips HeartModel;

(10) the term "controller" broadly encompasses all structural configurations of an application specific main board or an application specific integrated circuit for controlling an application of various principles of the present disclosure as subsequently exemplarily described herein. The structural configuration of the controller may include, but is not limited to, processor(s), computer-usable/computer readable storage medium(s), an operating system, application module(s), peripheral device controller(s), interface(s), bus(es), slot(s) and port(s). The labels "convolutional neural cardiac training", "convolutional neural cardiac diagnostic", "echo" and "ECG" as used herein for the term "controller" distinguishes for identification purposes a particular controller from other controllers as described and claimed herein without specifying or implying any additional limitation to the term "controller".

(11) the term "application module" broadly encompasses a component of an controller consisting of an electronic circuit and/or an executable program (e.g., executable software and/or firmware stored on non-transitory computer readable medium(s)) for executing a specific application. The labels "periodic volume generator" and "convolutional neural network" as used herein for the term "module" distinguishes for identification purposes a particular module from other modules as described and claimed herein without specifying or implying any additional limitation to the term "application module"; and

(12) the terms "signal", "data", and "command" broadly encompasses all forms of a detectable physical quantity or impulse (e.g., voltage, current, or magnetic field strength) as understood in the art of the present disclosure and as exemplary described herein for communicating information and/or instructions in support of applying various principles of the present disclosure as subsequently described herein. Signal/data/command communication between components of the present disclosure may involve any communication method, as known in the art of the present disclosure and hereinafter conceived, including, but not limited to, signal/data/command transmission/reception over any type of wired or wireless medium/datalink and a reading of signal/data/command uploaded to a computer-usable/computer readable storage medium.

The foregoing embodiments and other embodiments of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

DETAILED DESCRIPTION

Figure 1A:
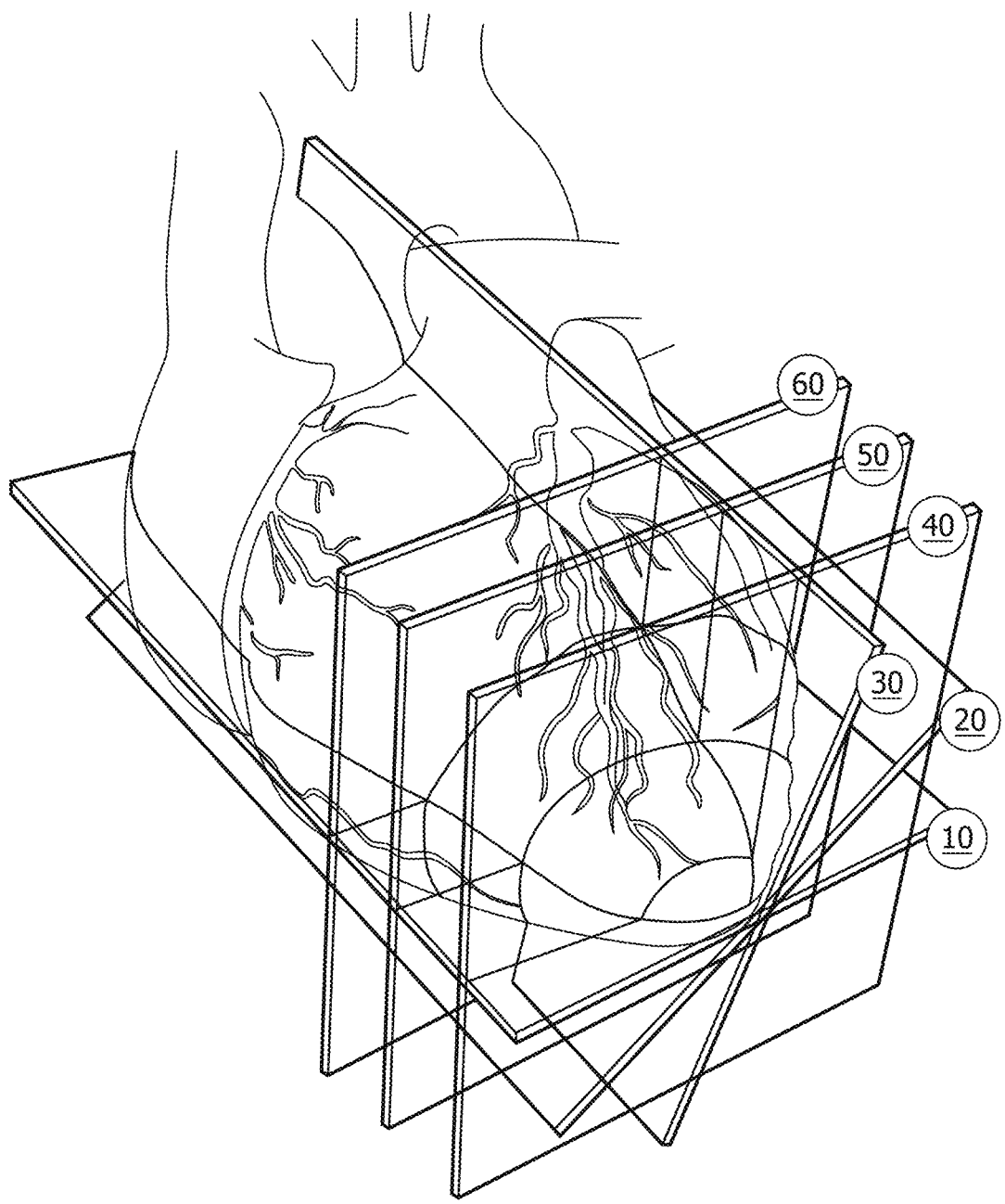
FIG. 1A illustrates six (6) views acquired in two-dimensional echocardiography as known in the art of the present disclosure.

The principles of the present disclosure are applicable to any type of cardiac diagnostic procedure including, but not limited to, echocardiography, cardiac CT, cardiac MRI, angiography, cardiac positron emission tomography (PET) and cardiac single photon computed emission tomography (SPECT). To facilitate an understanding of the principles of the present disclosure, the various embodiments of the present disclosure will be described in the context of an echocardiography application. From this description, those having ordinary skill in the art will appreciate how to apply the general principles of the present disclosure for any type of cardiac diagnostic procedure, other diagnostic procedure, or other image processing within or outside of the clinical realm.

In particular to echocardiography, FIG. 1 illustrates six (6) standard echocardiogram views consisting of a four chamber echocardiogram view 10, a two chamber echocardiogram view 20, a long axis echocardiogram view 30, a base echocardiogram view 40, a mid-echocardiogram view 50 and an apex echocardiogram view 60.

Figure 1B:
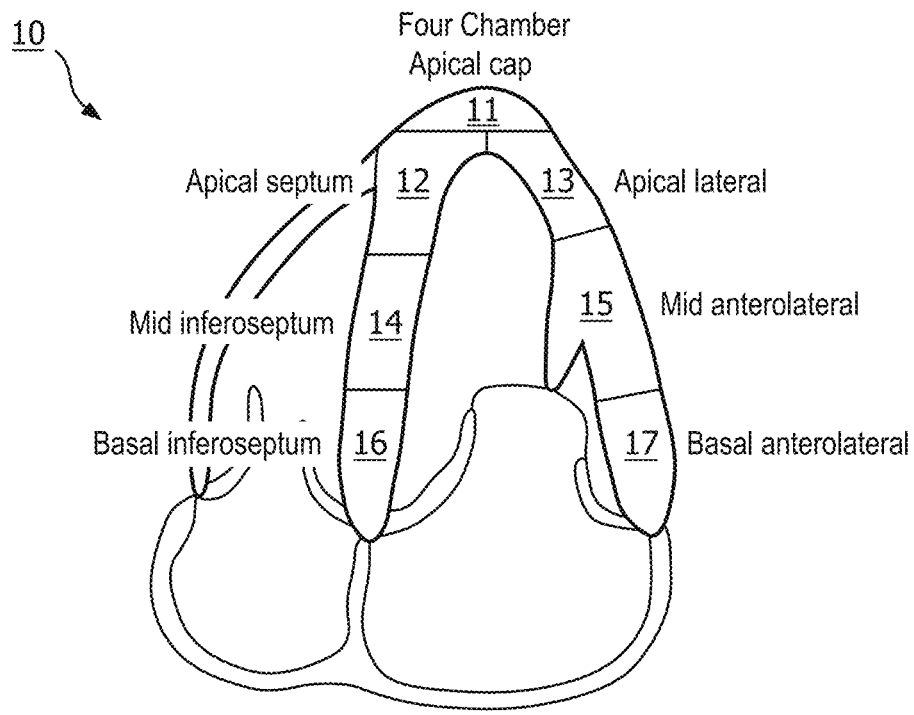
FIG. 1B illustrates a four chamber view acquired in two-dimensional echocardiography as known in the art of the present disclosure.

As shown in FIG. 1B, four chamber echocardiogram view 10 illustrates an apical cap segment 11, an apical septum segment 12, an apical lateral segment 13, a mid inferoseptum segment 14, a mid anterolateral segment 15, a basal inferoseptum 16 and a basal anteroplateral segment 17.

Figure 1C:
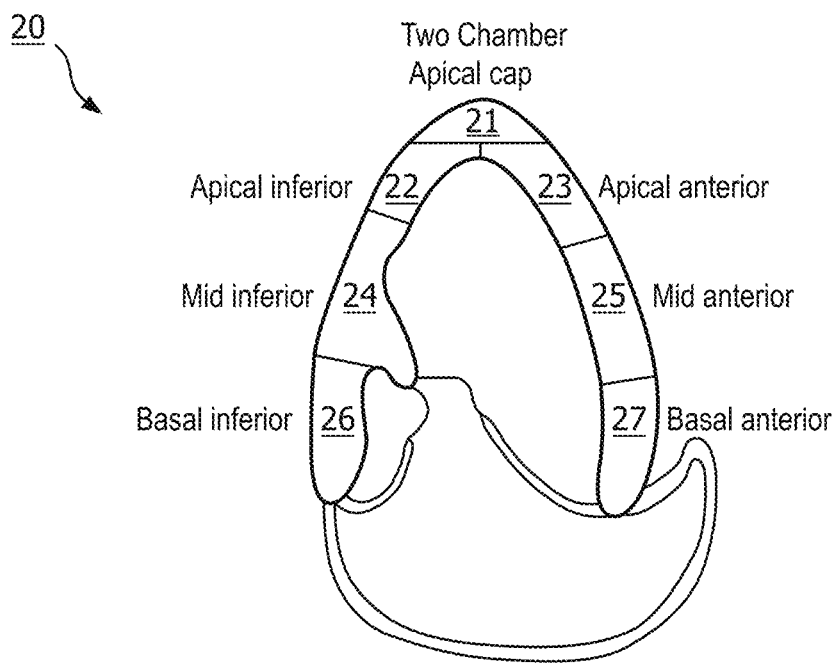
FIG. 1C illustrates a two chamber view acquired in two-dimensional echocardiography as known in the art of the present disclosure.

As shown in FIG. 1C, two chamber echocardiogram view 20 illustrates an apical cap segment 21, an apical inferior segment 22, an apical anterior segment 23, a mid inferior segment 24, a mid anterior segment 25, a basal inferior segment 26 and a basal anterior segment 27.

Figure 1D:
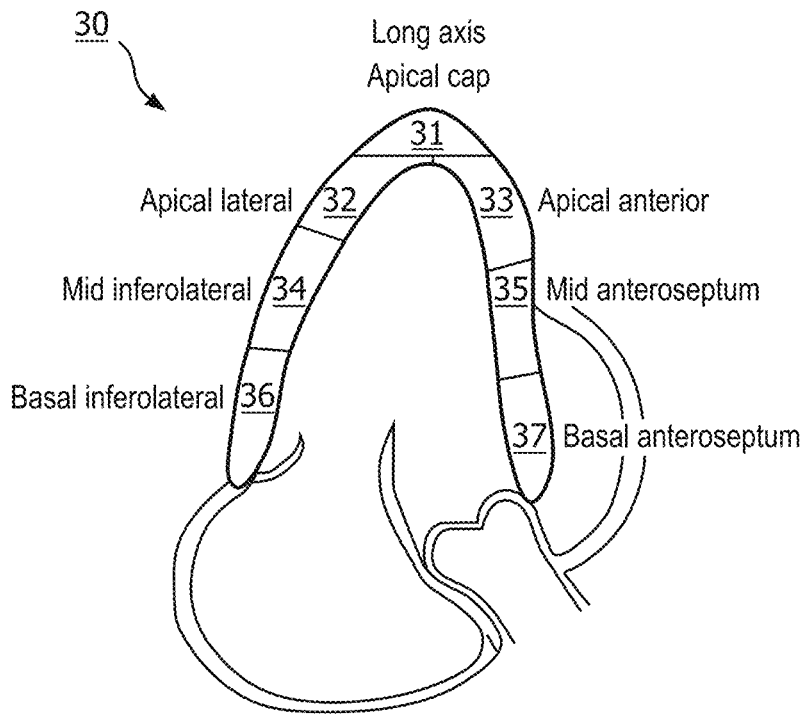
FIG. 1D illustrates long axis view acquired in two-dimensional echocardiography as known in the art of the present disclosure.

As shown in FIG. 1D, long axis echocardiogram view 30 illustrates an apical cap segment 31, an apical lateral segment 32, an apical septum segment 33, a mid inferolateral segment 34, a mid anteroseptum segment 35, a basal inferolateral 36 and a basal anteroseptum segment 37.

Figure 1E:
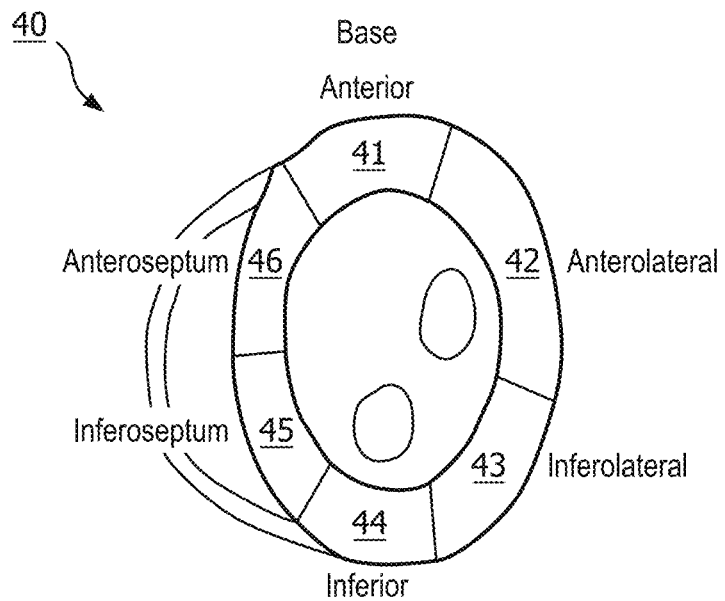
FIG. 1E illustrates base view acquired in two-dimensional echocardiography as known in the art of the present disclosure.

As shown in FIG. 1E, base echocardiogram view 40 illustrates an anterior segment 41, an anterolateral segment 42, an inferolateral segment 43, an inferior segment 44, an inferoseptum segment 45 and an anteroseptum segment 46.

Figure 1F:
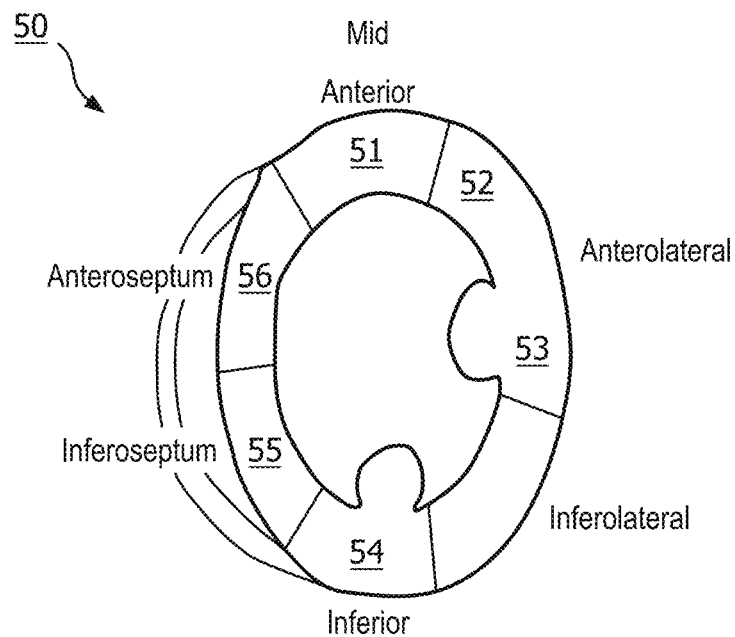
FIG. 1F illustrates mid view acquired in two-dimensional echocardiography as known in the art of the present disclosure.

As shown in FIG. 1F, mid echocardiogram view 50 illustrates an anterior segment 51, an anterolateral segment 52, an inferolateral segment 53, an inferior segment 54, an inferoseptum segment 55 and an anteroseptum segment 56.

Figure 1G:
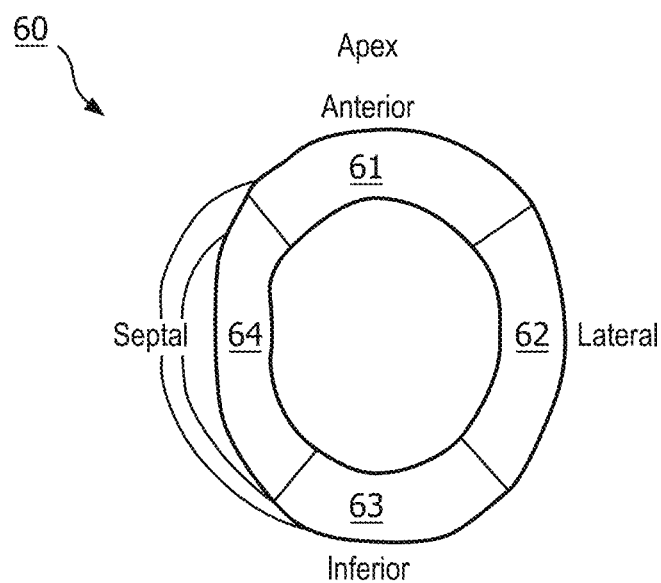
FIG. 1G illustrates apex view acquired in two-dimensional echocardiography as known in the art of the present disclosure.

As shown in FIG. 1G, apex echocardiogram view 60 illustrates an anterior segment 61, a lateral segment 62, an inferior segment 63 and a septal segment 64.

The embodiments of the present disclosure as applied to echocardiography provide for a detection and classification (quantification) of cardiovascular disease (CVD) involving an occlusion in one or more arteries, which results in contractility of one or more of the segments shown in FIGS. 1B-1G. More particularly, any abnormalities in cardiac wall motion are detected and classification(quantification) on a segment basis by a convolutional neural analysis of one or more of the echocardiogram views shown in FIG. 1A.

To facilitate an understanding of a convolutional neural cardiac training aspect of the embodiments of the present disclosure, the following description of FIGS. 2A-6B teaches general principles of an convolutional neural cardiac training of the present disclosure. From this description, those having ordinary skill in the art will appreciate how to apply the general principles of the present disclosure for implementing numerous and various embodiments of convolutional neural cardiac training of the present disclosure.

Figure 2A:
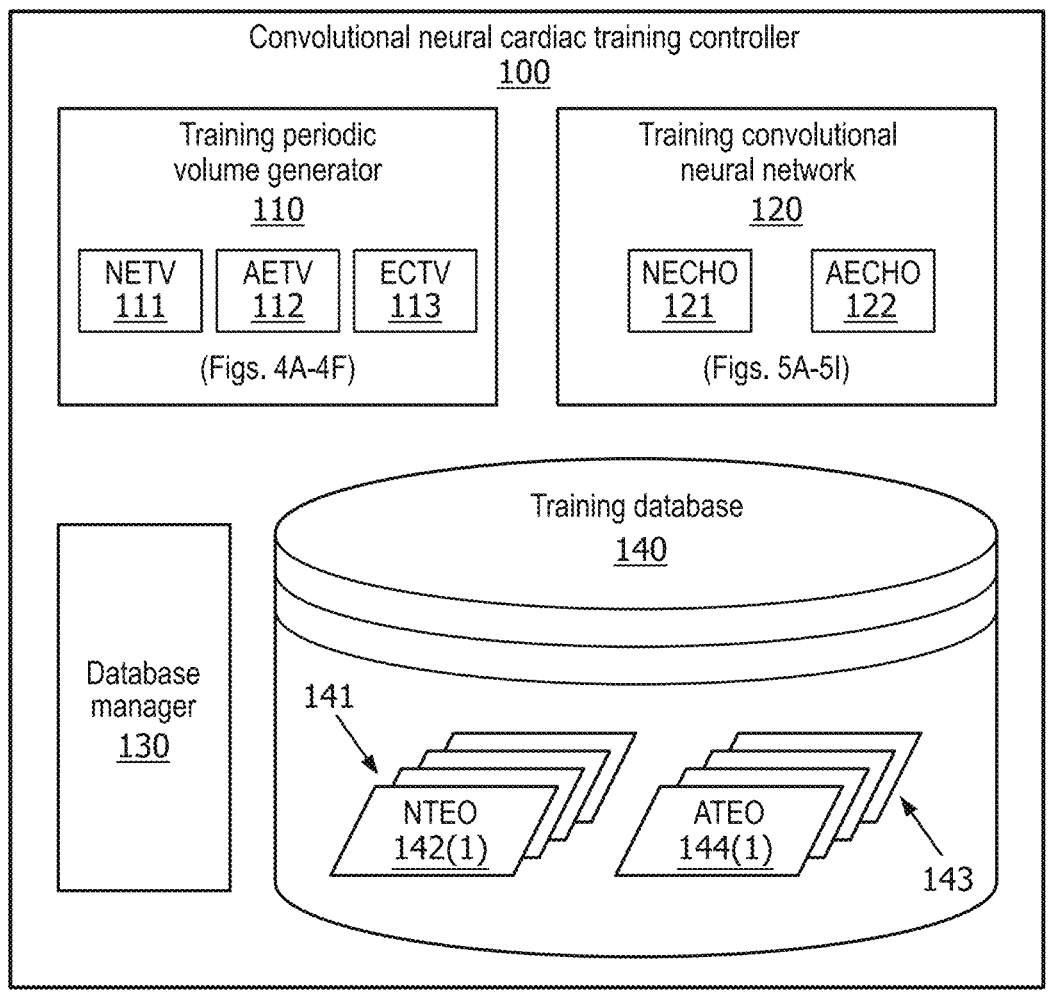
FIG. 2A illustrates an exemplary embodiment of a convolutional neural cardiac training controller in accordance with the principles of the present disclosure.

Referring to FIG. 2A, a convolutional neural cardiac training controller 100 employs a training periodic volume generator 110 and a training convolutional neural network 120 for training a detection and classification(quantification) of CVD, particularly on a segment basis. For training purposes, convolutional neural cardiac training controller 100 may further employ a database manager 130 and a training database 140 as shown, or alternatively be in communication with database manager 130 for purposes of accessing training database 140.

Training database 140 stores a set 141 of echocardiograms 142 demonstrating normal cardiac wall motion (and/or any other normal cardiac function) and a set 143 of echocardiograms 144 demonstrating abnormal cardiac wall motion (and/or any other abnormal cardiac function). Training database 140 may further store a set of electrocardiograms (not shown) corresponding to normal echocardiogram set 141, and a set of electrocardiograms (not shown) corresponding to abnormal echocardiogram set 142.

In practice, echocardiograms 143 and 144 may include a temporal sequence of 2D planar echo slices and/or a temporal sequence of 3D volume images.

Figure 2B:
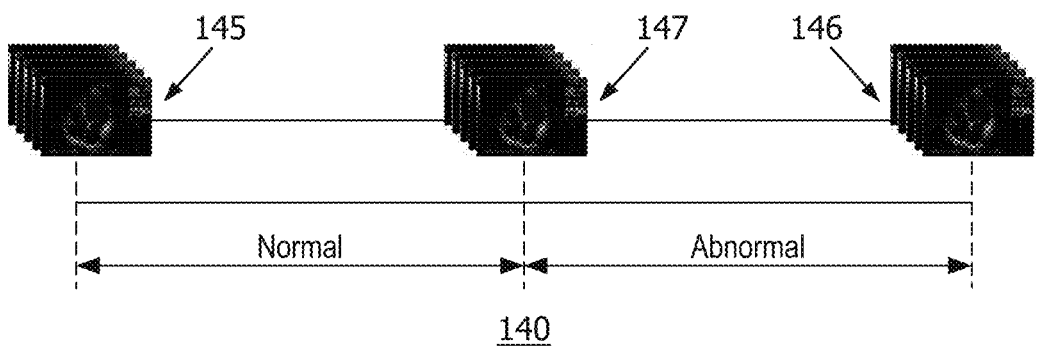
FIG. 2B illustrates an exemplary embodiment of objective echocardiogram scale in accordance with the principles of the present disclosure.

As shown in FIG. 2B, echocardiograms as stored on training database 140 may range on an echo scale 140 extending between an ideal normal echocardiogram 145 and a fatal abnormal echocardiogram 146 with a midline echocardiogram 147 representative of at a transitional state between a normal echocardiogram and an abnormal echocardiogram.

In practice, each normal echocardiograms 142 is positioned on echo scale 140 between deal normal echocardiogram 145 and midline echocardiogram 147 with a degree of cardiac wall motion normality, and each abnormal echocardiogram 144 is positioned on echo scale 140 between midline echocardiogram 147 and fatal abnormal echocardiogram 146 with a degree of cardiac wall motion abnormality.

Also in practice, set 141 of normal echocardiograms 142 and set 143 of abnormal echocardiograms 144 may include a single segmental echocardiogram view (FIG. 1A) or alternatively include subsets for two or more segmental echocardiogram views (FIG. 1A).

Referring back to FIG. 2A, training periodic volume generator 110 is an application module structurally configured to generate one or more normal echocardiogram training volume(s) 111 and one or more abnormal echocardiogram training volume(s) 112 in accordance with the principles of the present disclosure.

Specifically, in practice, each normal echocardiogram 142 and each abnormal echocardiogram 144 may include a temporal sequence of echocardiac cycles.

Figure 3A:
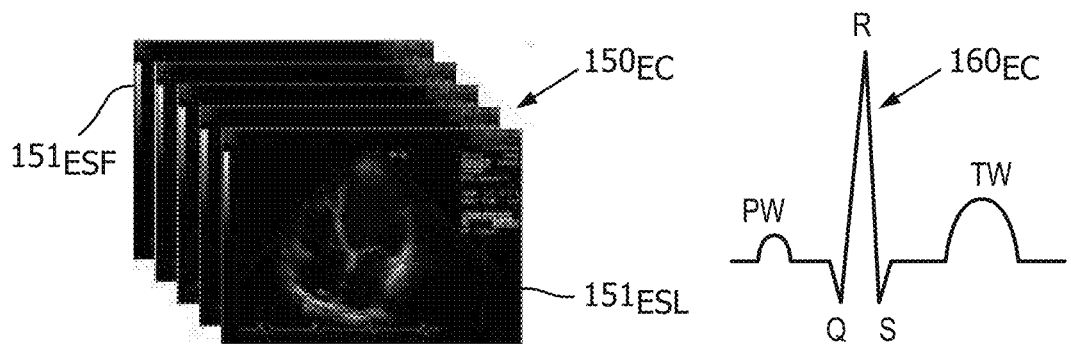
FIG. 3A illustrates an exemplary two-dimensional (2D) echocardiac cycle and an electrocardiac wave as known in the art of the present disclosure.

For example, FIG. 3A illustrates an echocardiac cycle $150_{EC}$ consisting of a temporal sequence of 2D planar echocardiac image slices over a single heartbeat extending between a first echocardiac slice $151_{ESF}$ and a last echocardiac slice $151_{ESL}$. Each echocardiogram 142 and each abnormal echocardiogram 144 includes a temporal sequence of echocardiac cycles $150_{EC}$. Training periodic volume generator 110 implement digital imaging processing technique(s) as known in the art of the present disclosure for a periodic stacking of the temporal sequence of echocardiac cycles $150_{EC}$ whereby a last echocardiac slice $151_{ESL}$ of any given echocardiac cycle $150_{EC}$ is a neighbor of a first echo echocardiac slice $151_{ESF}$ of any succeeding echocardiac cycle $150_{EC}$.

Figure 4A:
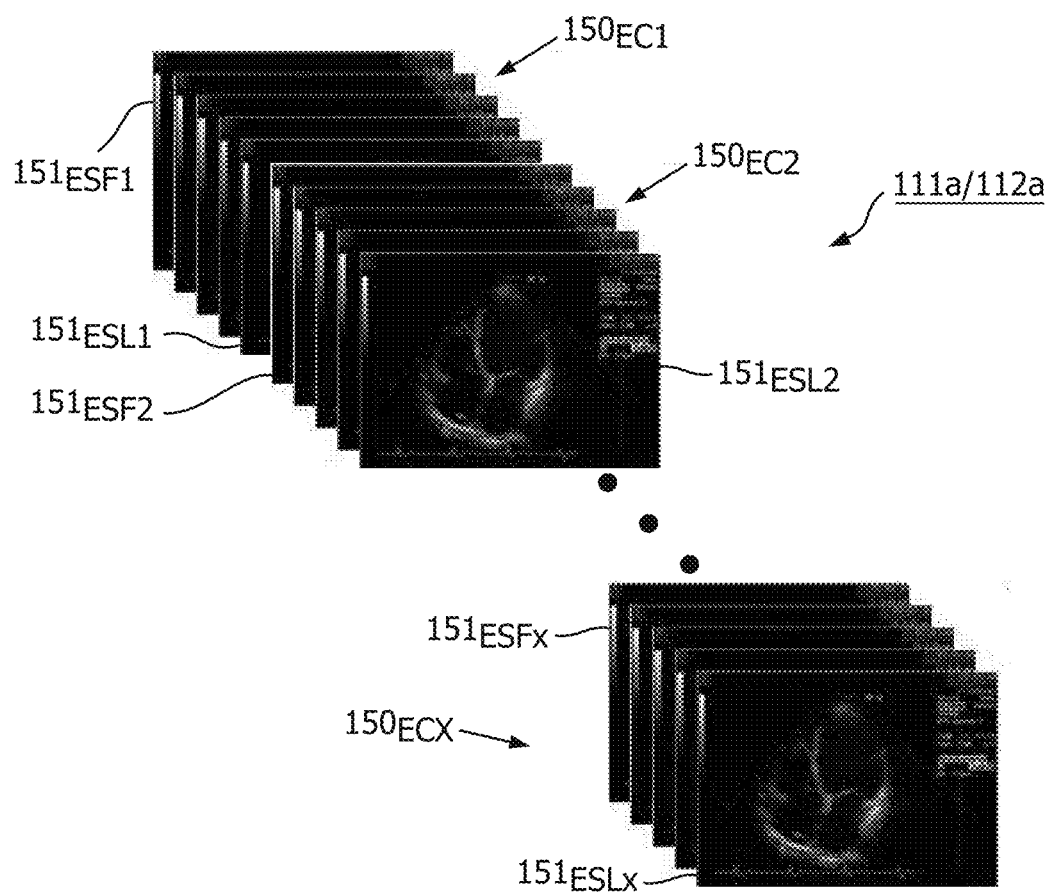
FIG. 4A illustrates an exemplary periodic stacking of 2D echocardiac cycles in accordance with the principles of the present disclosure.

For example, FIG. 4A illustrates a normal echocardiogram training volume 111a of the present disclosure derived from a periodic stacking of the temporal sequence of an X number of echocardiac cycle $150_{EC}$, X≥2, of a normal echocardiogram 142 whereby a last echocardiac slice $151_{ESL}$ of any given echocardiac cycle $150_{EC}$ is a neighbor of a first echo echocardiac slice $151_{ESF}$ of any succeeding echocardiac cycle $150_{EC}$.

Figure 4B:
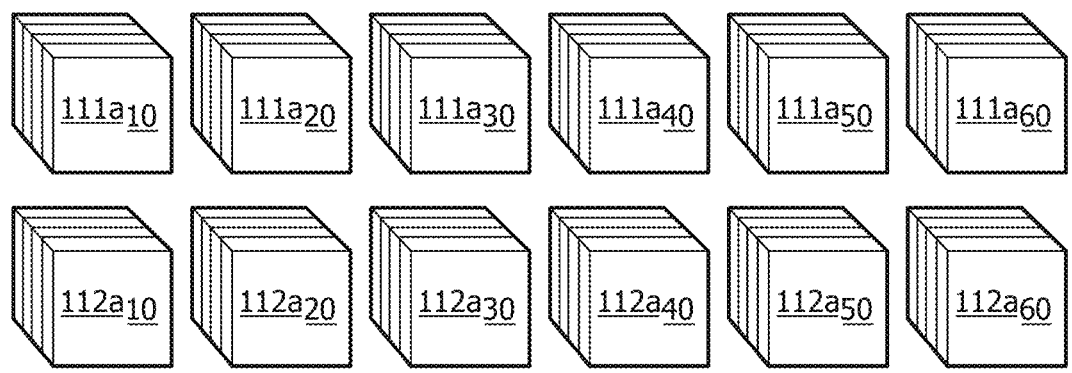
FIG. 4B illustrates a first exemplary set of echocardiogram training volumes in accordance with the principles of the present disclosure.
Figure 4C:
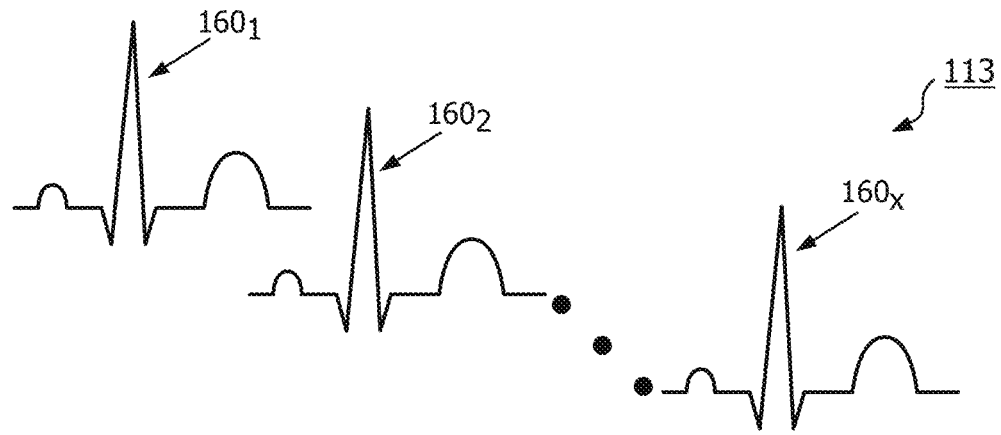
FIG. 4C illustrates an exemplary periodic stacking of electrocardiac waves in accordance with the principles of the present disclosure.

In practice, training periodic volume generator 110 generates a normal echocardiogram training volume 111a for one or more of the echocardiogram segmental views of a normal echocardiogram 142 whereby the normal echocardiogram training volume 111a may consist of a single degree or a multiple-degree of normality of a cardiac wall motion per scale 140 (FIG. 2B). For example, FIG. 4B illustrates six (6) normal echocardiogram training volumes 111a corresponding to the six (6) echocardiogram segmental views of FIG. 1A.

Similarly, FIG. 4A illustrates an abnormal echocardiogram training volume 112a of the present disclosure derived from a periodic stacking of the temporal sequence of an X number of echocardiac cycle $150_{EC}$, X≥2, of an abnormal echocardiogram 144 whereby a last echocardiac slice $151_{ESL}$ of any given echocardiac cycle $150_{EC}$ is a neighbor of a first echo echocardiac slice $151_{ESF}$ of any succeeding echocardiac cycle $150_{EC}$.

In practice, training periodic volume generator 110 generates an abnormal echocardiogram training volume 112a for one or more of the echocardiogram segmental views of an abnormal echocardiogram 144 whereby the abnormal echocardiogram training volume 112a may consist of a single degree or a multiple-degree of normality of a cardiac wall motion per scale 140 (FIG. 2B). For example, FIG. 4B illustrates six (6) abnormal echocardiogram training volumes 112a corresponding to the six (6) echocardiogram segmental views of FIG. 1A.

Referring back to FIG. 2A, training periodic volume generator 110 may be further structurally configured to generate one or more electrocardiogram training volume(s) 113 in accordance with the principles of the present disclosure.

Specifically, as previously described, training database 140 may store an electrocardiogram corresponding to each normal echocardiogram 142 and each abnormal echocardiogram 144 whereby each electrocardiogram includes a temporal sequence of ECG waves.

Figure 3B:
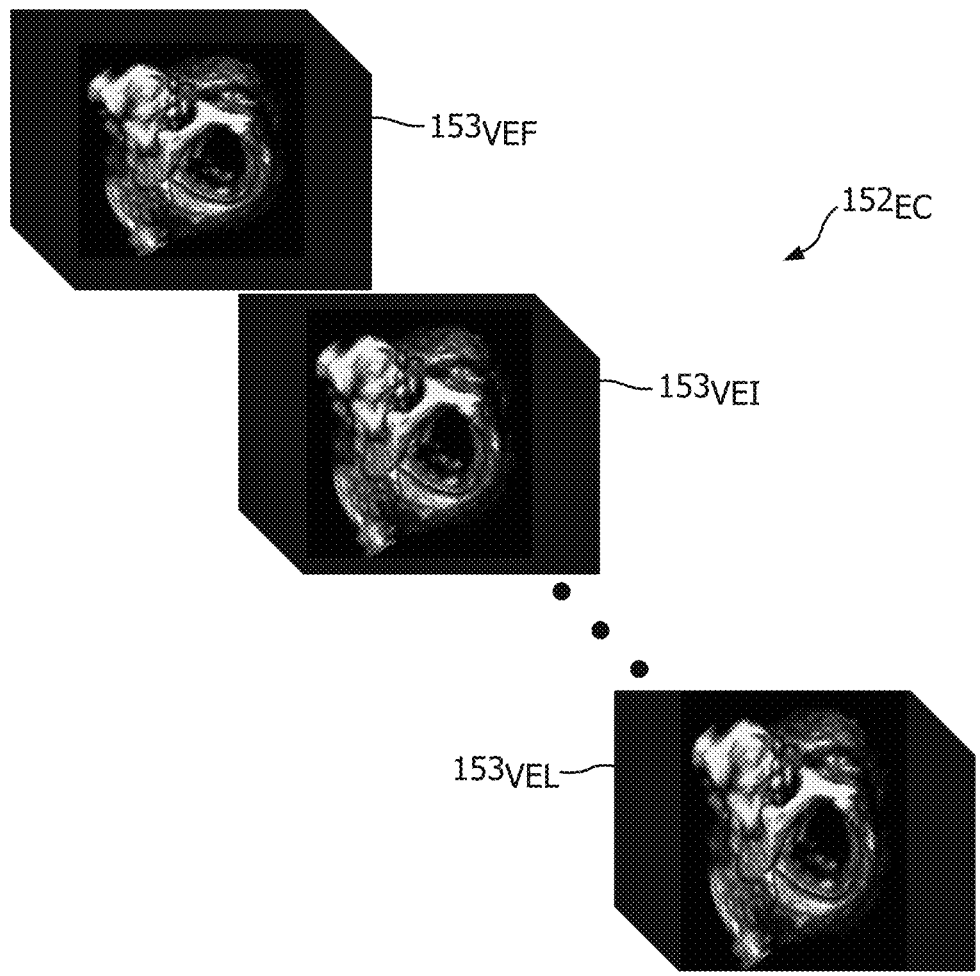
FIG. 3B illustrates an exemplary three-dimensional (3D) echocardiac cycle as known in the art of the present disclosure.

For example, FIG. 3 illustrates an ECG wave $160_{CC}$ over a single heartbeat. Training periodic volume generator 110 implement digital imaging processing technique(s) as known in the art of the present disclosure for a periodic stacking of the temporal sequence of ECG waves 160. For example, FIG. 4A illustrates an electrocardiogram training volume 113a of the present disclosure derived from a periodic stacking of the temporal sequence of an X number of ECG waves $160_{CC}$, X≥2.

Figure 4D:
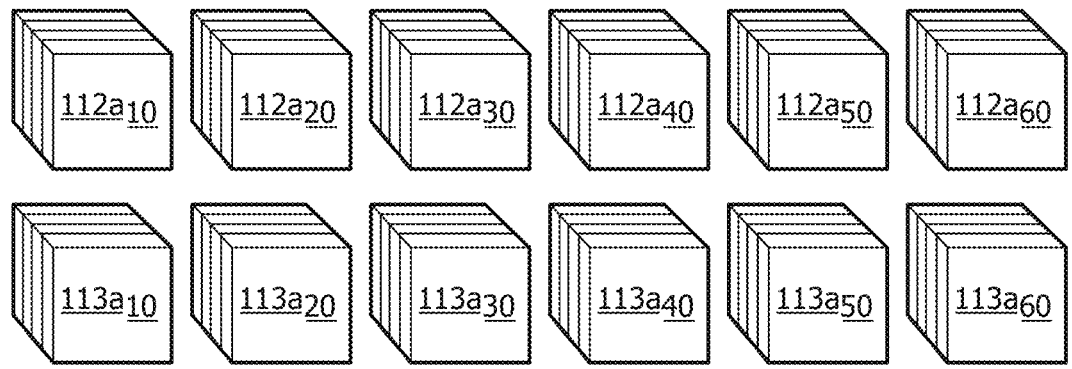
FIG. 4D illustrates an exemplary set of echocardiogram training volumes and of electrocardiogram training volumes in accordance with the principles of the present disclosure.

Referring back to FIG. 2A, in practice, training periodic volume generator 110 may generate an electrocardiogram training volume 113a for each generated normal echocardiogram training volume 111 and each generated abnormal volume 112. For example, FIG. 4D illustrates six (6) abnormal echocardiogram training volume 112a for the six (6) echocardiogram segmental views of FIG. 1A with each abnormal echocardiogram training volume 112a having a corresponding electrocardiogram training volume 113a.

Referring back to FIG. 2, in practice, each normal echocardiogram 142 and each abnormal echocardiogram 144 as stored in training database 140 may alternatively include a temporal sequence of echocardiac cycles of three-dimensional (3D) volumetric echocardiac images.

For example, FIG. 3A illustrates an echocardiac cycle $152_{EC}$ consisting of a temporal sequence of 3D volumetric echocardiac images 153 over a single heartbeat extending between a first volumetric echocardiac image $153_{VEF}$ and a last volumetric echocardiac image $151_{VEL}$. Each echocardiogram 142 and each abnormal echocardiogram 144 includes a temporal sequence of echocardiac cycles $152_{EC}$. Training periodic volume generator 110 implement digital imaging processing technique(s) as known in the art of the present disclosure for a periodic stacking of the temporal sequence of echocardiac cycles $152_{EC}$ whereby a last volumetric echocardiac image $153_{ESF}$ of any given echocardiac cycle $152_{EC}$ is a neighbor of a first volumetric echocardiac image $151_{ESF}$ of any succeeding echocardiac cycle $152_{EC}$.

Figure 4E:
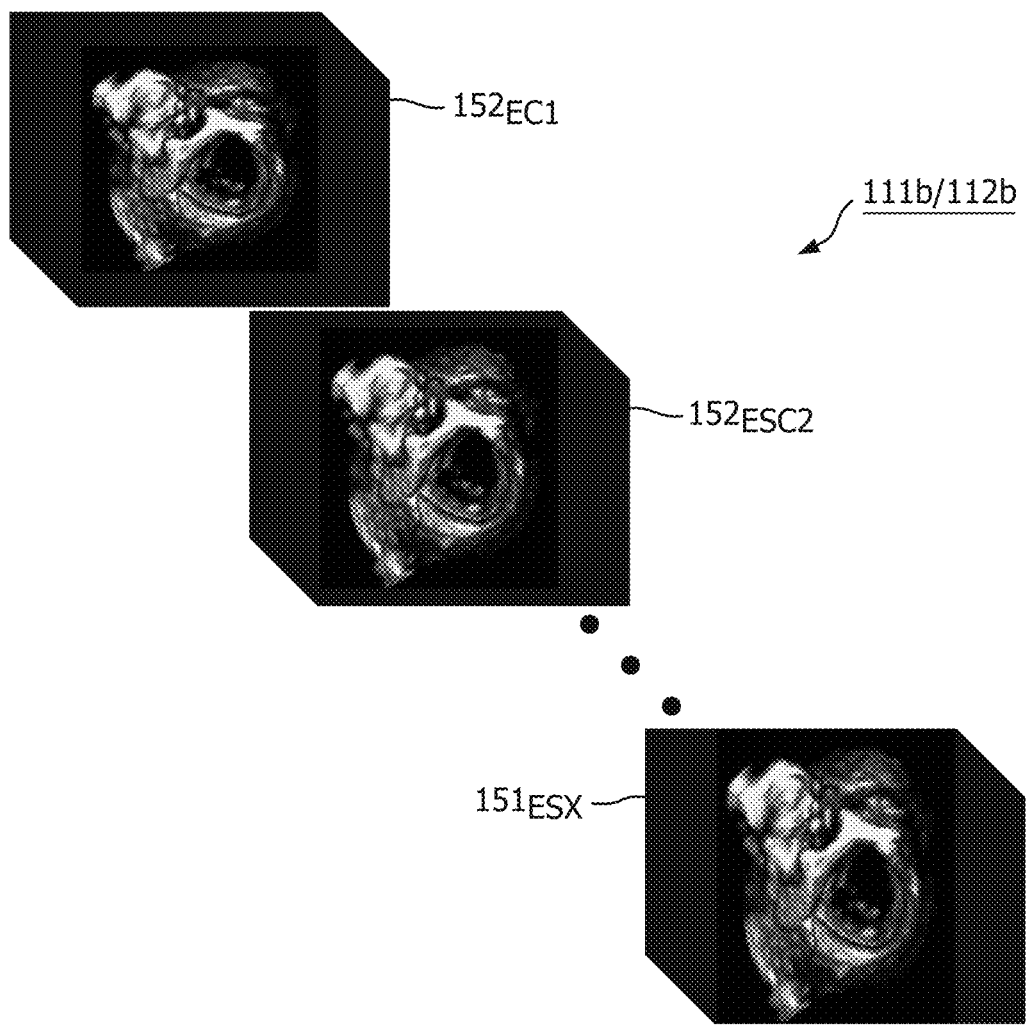
FIG. 4E illustrates an exemplary periodic stacking of 3D echocardiac cycles in accordance with the principles of the present disclosure.

For example, FIG. 4E illustrates an X number of echocardiac cycles $152_{EC}$, X≥2, extending over one or more beats. Training periodic volume generator 110 implement digital imaging processing technique(s) as known in the art of the present disclosure for a periodic stacking of the temporal sequence of echocardiac cycles $152_{EC}$ 152 to form a normal echocardiogram training volume 111b from a normal 3D echocardiogram 142 or an abnormal echocardiogram training volume 112b from an abnormal 3D echocardiogram 144.

Figure 4F:
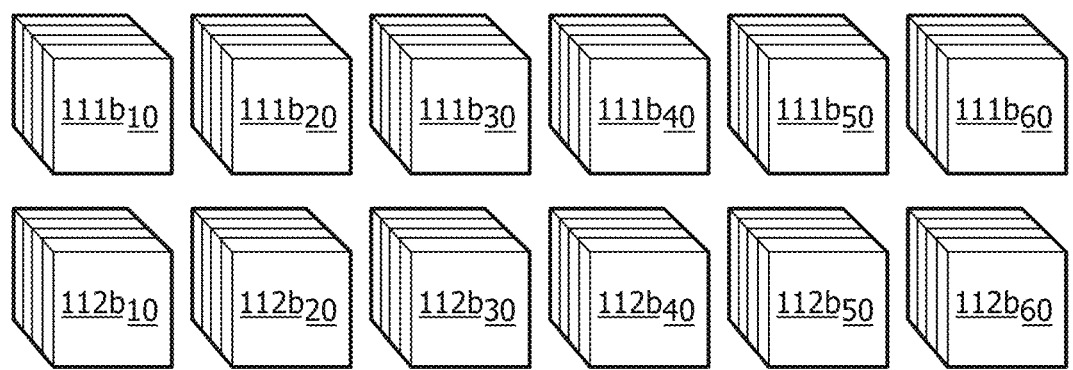
FIG. 4F illustrates a second exemplary set of echocardiogram training volumes in accordance with the principles of the present disclosure.

In practice, training periodic volume generator 110 generates a normal echocardiogram training volume 111b for one or more of the echocardiogram segmental views of a normal 3d echocardiogram 142 whereby the normal echocardiogram training volume 111b may consist of a single degree or a multiple-degree of normality of a cardiac wall motion per scale 140 (FIG. 2B). For example, FIG. 4F illustrates six (6) normal echocardiogram training volume 111b for the six (6) echocardiogram segmental views of FIG. 1A.

Similarly in practice, training periodic volume generator 110 generates an abnormal echocardiogram training volume 112b for one or more of the echocardiogram segmental views of an abnormal 3D echocardiogram 144 whereby the abnormal echocardiogram training volume 112b may consist of a single degree or a multiple-degree of abnormality of a cardiac wall motion per scale 140 (FIG. 2B). For example, FIG. 4F illustrates six (6) normal echocardiogram training volume 112a for the six (6) echocardiogram segmental views of FIG. 1A.

Also in practice, electrocardiogram training volumes 113a (FIG. 4C) may be co-generated with volumes 111b/112b as previously described in the present disclosure for volumes 111a/112b (FIG. 4A).

Referring back to FIG. 2A, training convolutional neural network (CNN) 120 is an application module structurally configured for processing a normal echocardiogram training volume 111 to generate a normal echocardiogram classifier 121 indicative of a normal cardiac wall motion, and for processing an abnormal echocardiogram training volume 112 to output an abnormal echocardiogram classifier 122 indicative of an abnormal cardiac wall motion. If corresponding electrocardiograms are utilized, training CNN 120 processes volumes 111 and 113 to output normal echocardiogram classification 121, and training CNN 120 processes volumes 112 and 113 to output abnormal echocardiogram classification.

In practice, training CNN 120 may execute any type of CNN known in the art of the present disclosure for delineating a connectivity pattern between motion features of volumes 111, 112 and 113 (if applicable) that facilitates a classification of motion within volumes 111, 112 and 113 (if applicable).

In one embodiment, training CNN 120 executes a basic spatial-temporal CNN involving a connectivity between layers via local filters, and a parameter sharing via convolutions. In the training process, the CNN is learned to recognize patterns in the echo images (and ECG) which is indicative of the cardiac abnormalities. The type of abnormality that CNN is trained to recognize is defined during the training process by using training cases (images and ECG signals) with the abnormality present. The training can be commenced either with or without ECG signal depending on availability of ECG data.

Figure 5A:
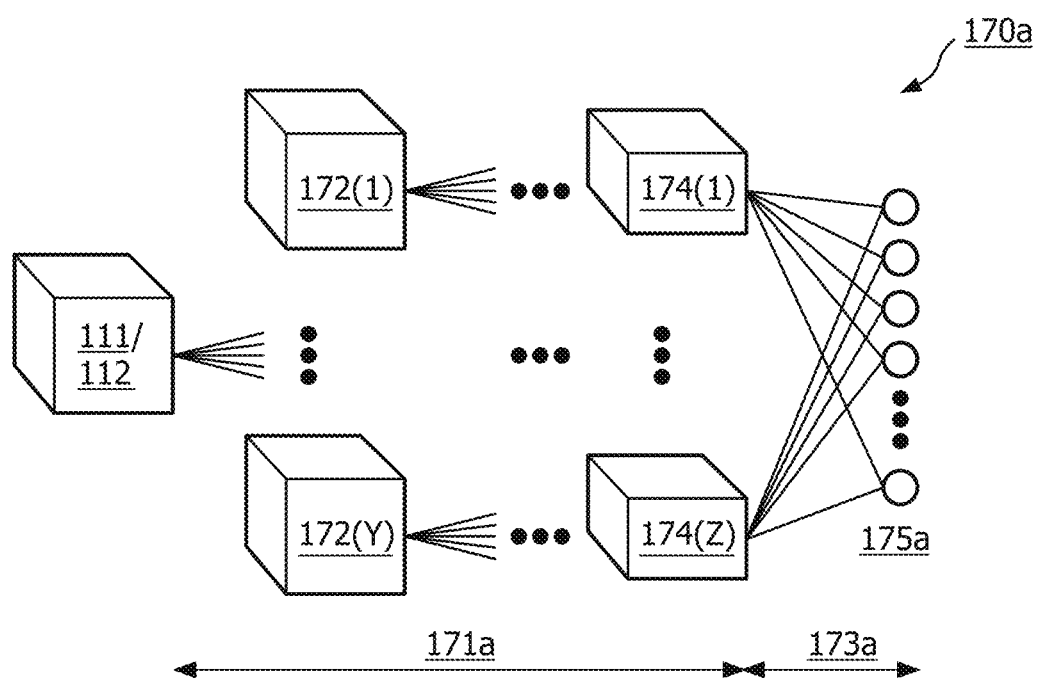
FIG. 5A illustrates an exemplary spatial-temporal based convolutional neural analysis of an echocardiogram training volume in accordance with the principles of the present disclosure.

For example, FIG. 5A illustrates a training CNN 170a for processing a segmental view of a normal echocardiogram training volume 111 or of an abnormal echocardiogram training volume 112 involving a 3D convolution and subsampling stage 171a of filters 172 and 174 for combining spatial and temporal information of volume 111 or volume 112 to establish a fully connected stage 173a of motion features 175a for classification. In practice, a particular setup of training CNN 170a in terms of the number and types of layers and kernels will be dependent upon (1) a size of volume 111 or of volume 112 (whichever is being processed), (2) a desired detection accuracy of CNN 170a and (3) a type of abnormality that CNN 170a is designed to classify/quantify.

Figure 5B:
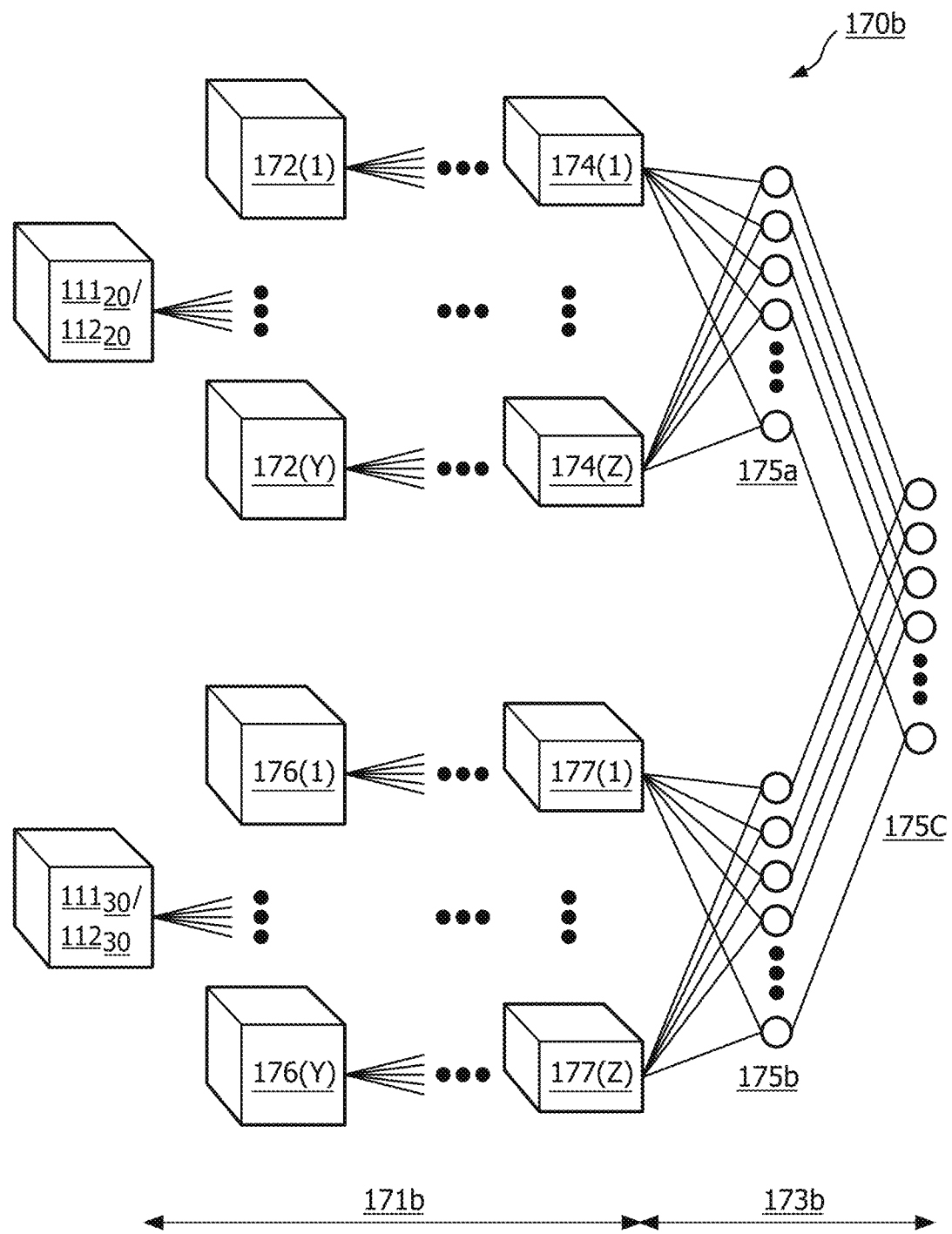
FIG. 5B illustrates an exemplary spatial-temporal based convolutional neural analysis of a pair of echocardiogram training volumes in accordance with the principles of the present disclosure.

By further example, FIG. 5B illustrates a training CNN 170b for processing an additional segmental view of a normal echocardiogram training volume 111 or of an abnormal echocardiogram training volume 112 involving a 3D convolution and subsampling stage 171b of filters 176 and 177 for combining spatial and temporal information of the additional volume 111 or volume 112 to establish a fully connected stage 173b of motion features 175a and motion features 175b to output motion features 175c for classification. In practice, a particular setup of training CNN 170b in terms of the number and types of layers and kernels will be dependent upon (1) a size of volumes 111 or of volumes 112 (whichever is being processed), (2) a desired detection accuracy of CNN 170b and (3) a type of abnormality that CNN 170b is designed to classify/quantify.

Figure 5C:
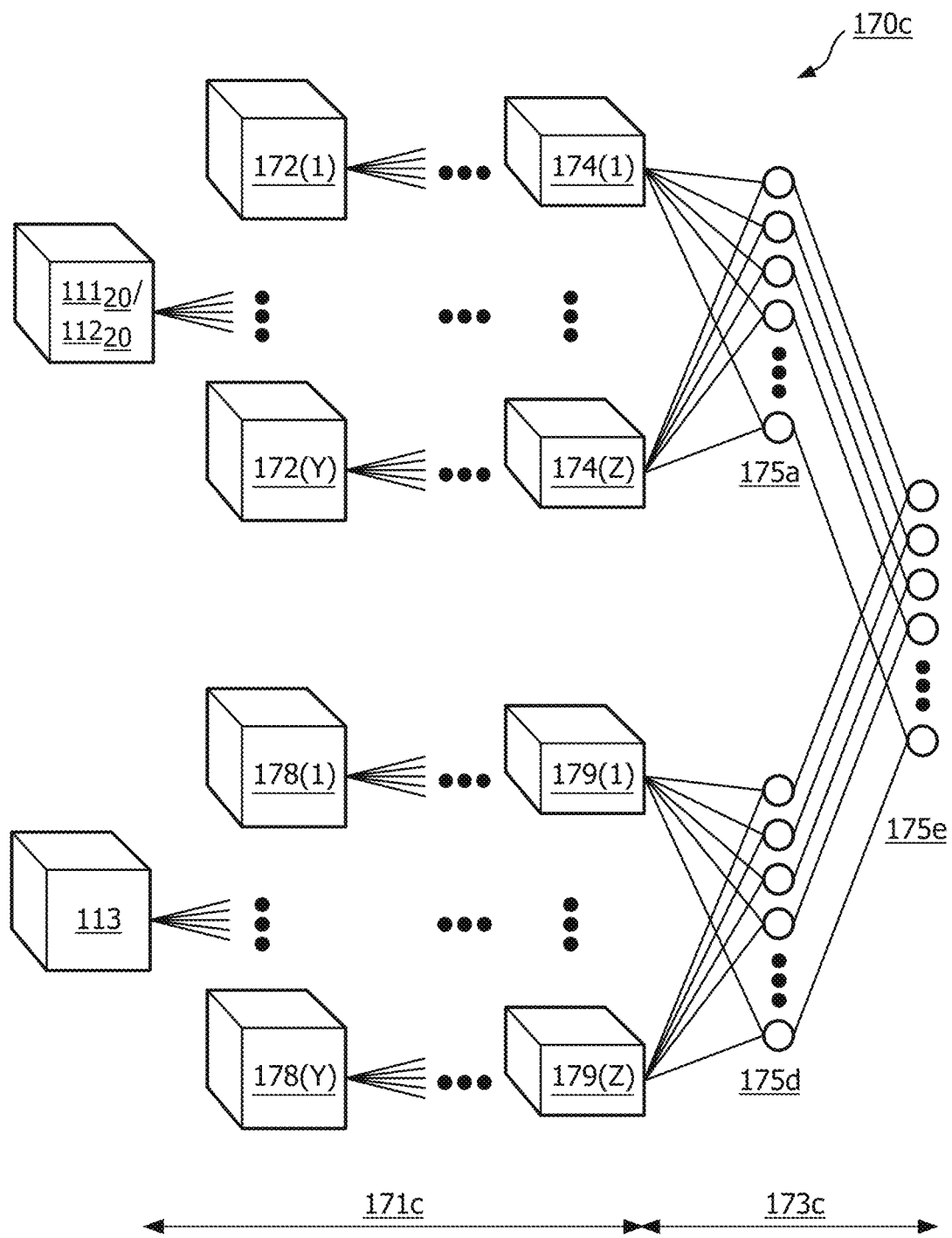
FIG. 5C illustrates an exemplary spatial-temporal based convolutional neural analysis of an echocardiogram training volume and an electrocardiogram training volume in accordance with the principles of the present disclosure.

By further example, FIG. 5C illustrates a training CNN 170c for additionally processing an electrocardiogram training volume 113 involving a 3D convolution and subsampling stage 171c of filters 178 and 179 for combining spatial and temporal information of volume 113 to establish a fully connected stage 173c of motion features 175a and wave features 175d to output motion features 175e for classification. In practice, a particular setup of training CNN 170c in terms of the number and types of layers and kernels will be dependent upon (1) a size of volumes 111/113 or of volumes 112/113 (whichever is being processed), (2) a desired detection accuracy of CNN 170c and (3) a type of abnormality that CNN 170c is designed to classify/quantify.

Referring back to FIG. 2A, in a second embodiment, training CNN 120 executes a multiple stream CNN involving an execution of a spatial-temporal CNN for each echocardiogram slice of a normal echocardiogram training volume 111 or an abnormal echocardiogram training volume 112 (i.e., a spatial stream CNN) and an execution of spatial-temporal CNN for a motion flow of normal echocardiogram training volume 111 or abnormal echocardiogram training volume 112 (i.e., a temporal stream CNN). The multiple (dual) streams are combined by a late fusion of scores (e.g., an averaging a linear SVM, another neural network). The information from the multiple (dual) streams can also be combines by using shared convolutional kernels between different streams.

Figure 5D:
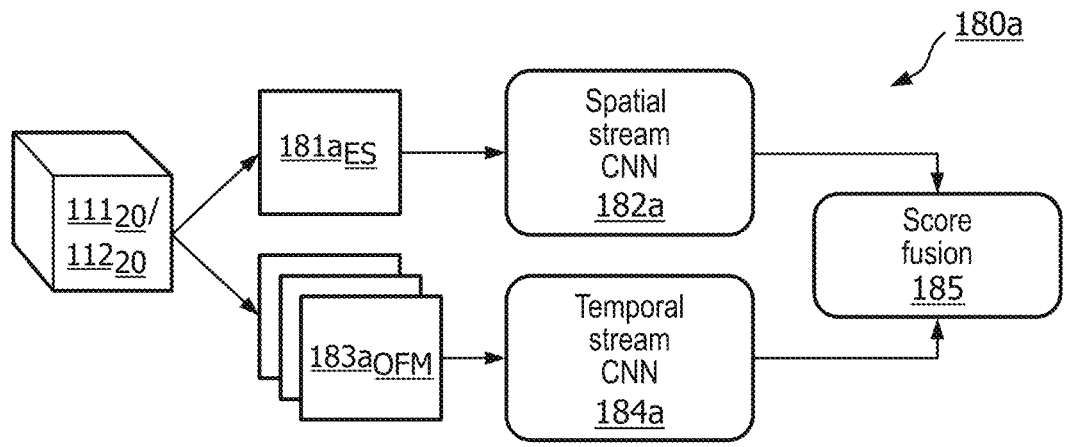
FIG. 5D illustrates an exemplary multiple stream based convolutional neural analysis of an echocardiogram training volume in accordance with the principles of the present disclosure.

For example, FIG. 5D illustrates a training CNN 180a for executing a spatial stream CNN 182a for each eco echocardiogram slice 181a of a segmental view of a normal echocardiogram training volume 111 or of an abnormal echocardiogram training volume 112, and for executing a temporal stream CNN 184a for a motion flow 183a of volume 111 or of volume 112. The multiple streams 182a and 184a are combined by a late score fusion 186. In practice, a particular setup of training CNN 180a in terms a complexity of spatial stream CNN 182a and temporal stream CNN 184a will be dependent upon (1) a size of volume 111 or of volume 112 (whichever is being processed), (2) a desired detection accuracy of CNN 180a and (3) a type of abnormality that CNN 180b is designed to classify/quantify.

Figure 5E:
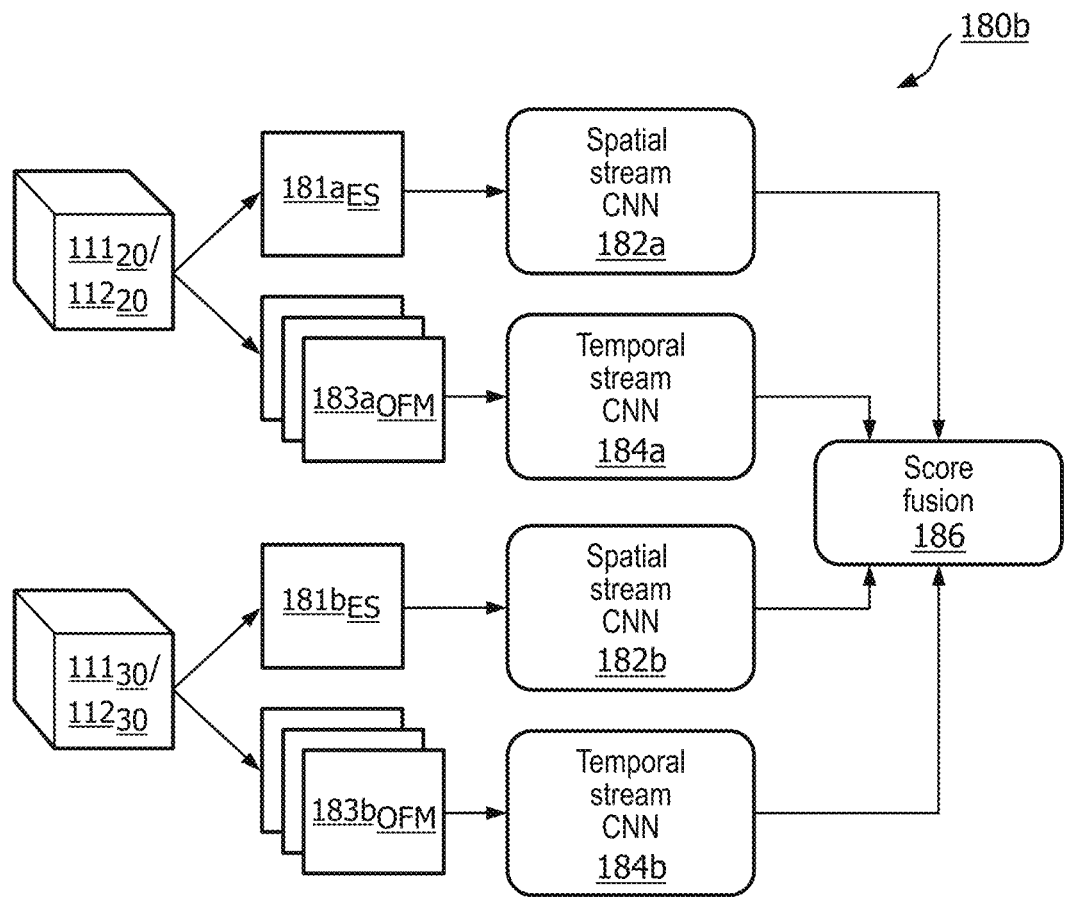
FIG. 5E illustrates an exemplary multiple stream based convolutional neural analysis of a pair of echocardiogram training volumes in accordance with the principles of the present disclosure.

By further example, FIG. 5E illustrates a training CNN 180b for executing a spatial stream CNN 182b for each eco echocardiogram slice 181b of an additional segmental view of a normal echocardiogram training volume 111 or of an abnormal echocardiogram training volume 112, and for executing a temporal stream CNN 184b for a motion flow 183b of the additional volume 111 or of the additional volume 112. The multiple streams 182a and 184a and the multiple streams 182b and 184b are combined by a late score fusion 186. In practice, a particular setup of training CNN 180b in terms a complexity of spatial stream CNNs 182a and 182b and of temporal stream CNN 184a and 184b will be dependent upon (1) a size of volumes 111 or of volumes 112 (whichever is being processed), (2) a desired detection accuracy of CNN 180b and (3) a type of abnormality that CNN 180b is designed to classify/quantify.

Figure 5F:
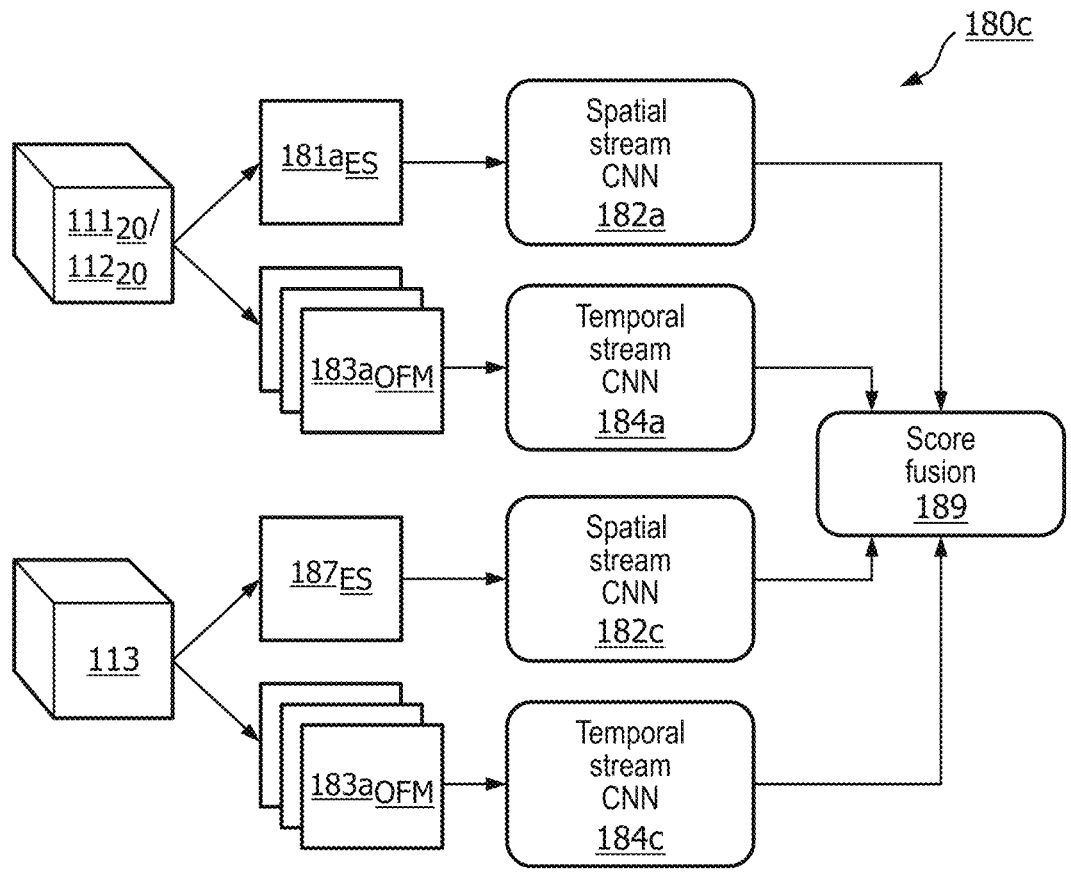
FIG. 5F illustrates an exemplary multiple stream based convolutional neural analysis of an echocardiogram training volume and an electrocardiogram training volume in accordance with the principles of the present disclosure.

By further example, FIG. 5F illustrates a training CNN 180c for executing a spatial stream CNN 182c for each electrocardiac wave 187 of an electrocardiogram training volume 113, and for executing a temporal stream CNN 184b for a wave flow 188 of volume 113. The multiple streams 182a and 184a and the multiple streams 182c and 184c are combined by a late score fusion 189. In practice, a particular setup of training CNN 180b in terms of a complexity of spatial stream CNNs 182a and 182c and of temporal stream CNN 184a and 184c will be dependent upon (1) a size of volumes 111/113 or of volumes 112/113 (whichever is being processed), (2) a desired detection accuracy of CNN 170c and (3) a type of abnormality that CNN 170c is designed to classify/quantify.

Referring back to FIG. 2A, in a third embodiment, training CNN 120 executes a memory recurrent CNN involving an execution of a spatial-temporal CNN for each echocardiogram slice or a sliced 3D volume of a normal echocardiogram training volume 111 or an abnormal echocardiogram training volume 112, a mean polling of the outputs of the spatial temporal CNNs, and an execution of a recurrent neural network (RNN) of the mean polling to obtain a scoring output.

Figure 5G:
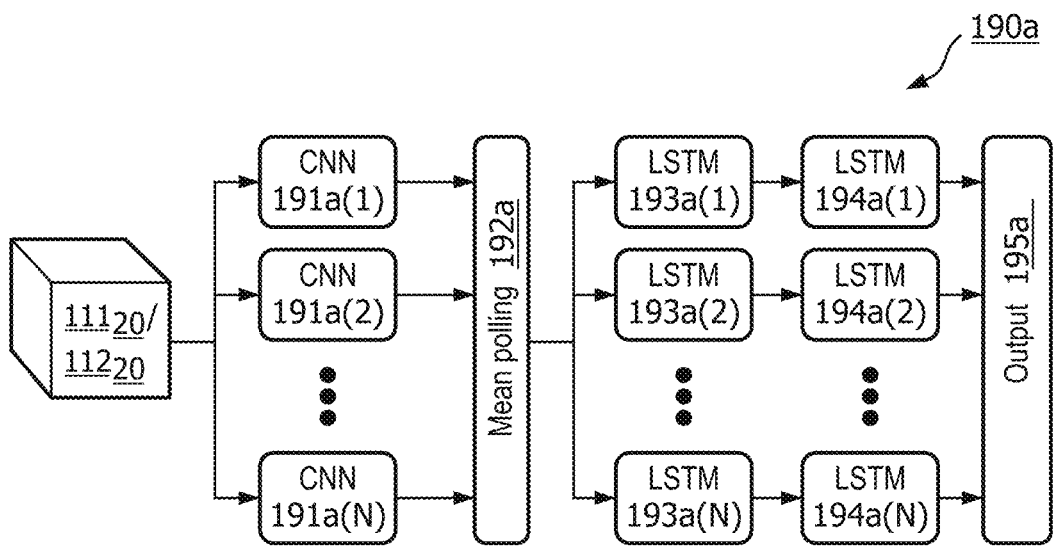
FIG. 5G illustrates an exemplary memory recurrent based convolutional neural analysis of an echocardiogram training volume in accordance with the principles of the present disclosure.

For example, FIG. 5G illustrates a memory recurrent CNN 190a involving an execution of a mean polling 192a of a spatial-temporal CNN 191a for each echocardiogram slice of a segmental view of a normal echocardiogram training volume 111 or an abnormal echocardiogram training volume 112, followed by an execution of a Long Short Term Memory (LSTM) RNN 193a and LSTM RNN 194a to obtain a scoring output 195a. In practice, a particular setup of training CNN 190a in terms of a complexity of spatial-temporal CNN 191a, LSTM RNN 193a and LSTM RNN 194a will be dependent upon (1) a size of volume or of volume 112 (whichever is being processed), (2) a desired detection accuracy of CNN 190a and (3) a type of abnormality that CNN 190a is designed to classify/quantify.

Figure 5H:
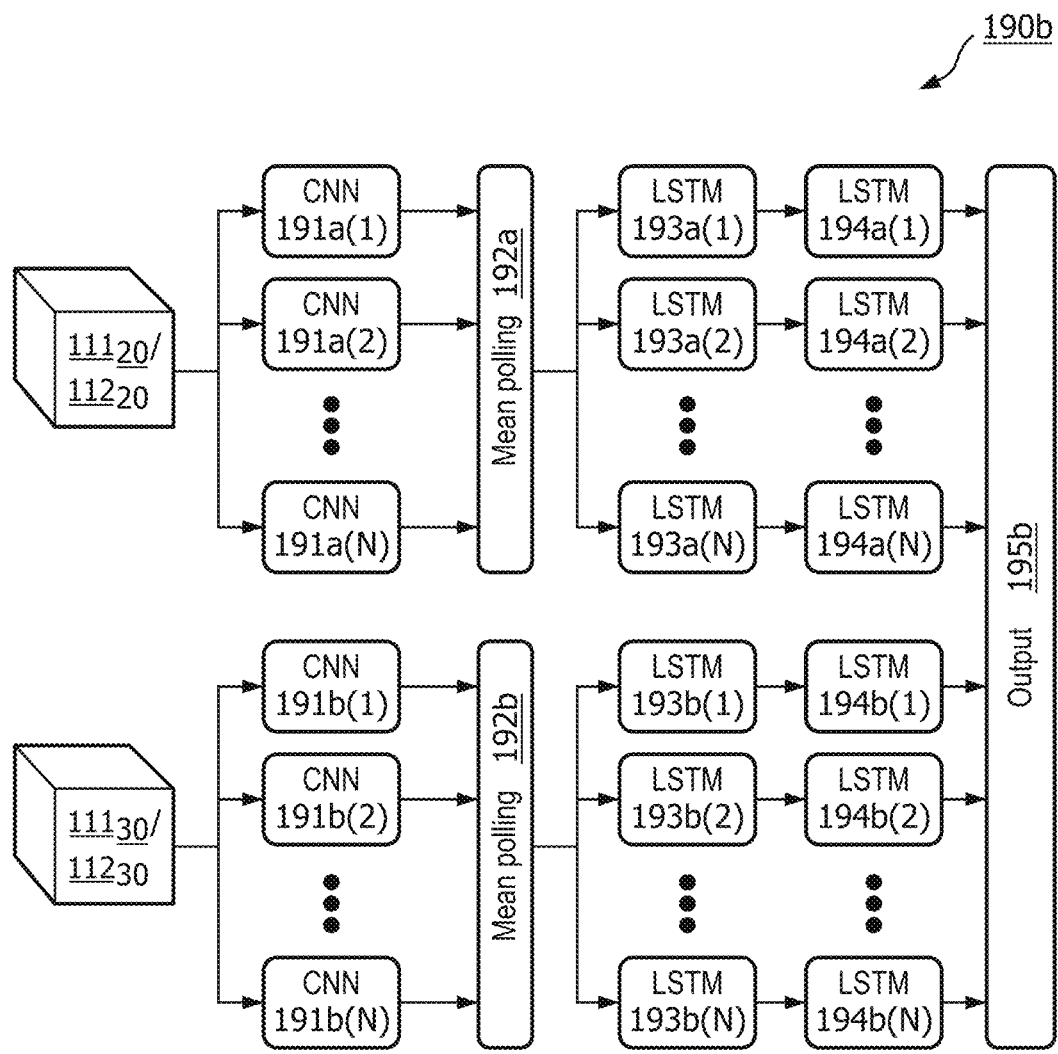
FIG. 5H illustrates an exemplary memory recurrent based convolutional neural analysis of a pair of echocardiogram training volumes in accordance with the principles of the present disclosure.

By further example, FIG. 5H illustrates a memory recurrent CNN 190b involving an execution of a mean polling 192b of a spatial-temporal CNN 191b for each echocardiogram slice of an additional segmental view of a normal echocardiogram training volume 111 or an abnormal echocardiogram training volume 112, followed by an execution of a Long Short Term Memory (LSTM) RNN 193b and LSTM RNN 194b to obtain a scoring output 195b. In practice, a particular setup of training CNN 190b in terms of a complexity of spatial-temporal CNNs 191a and 191b, and LSTM RNNs 193a, 193b, 194a and 194b will be dependent upon (1) a size of volumes 111 or of volumes 112 (whichever is being processed), (2) a desired detection accuracy of CNN 190b and (3) a type of abnormality that CNN 190b is designed to classify/quantify.

Figure 5I:
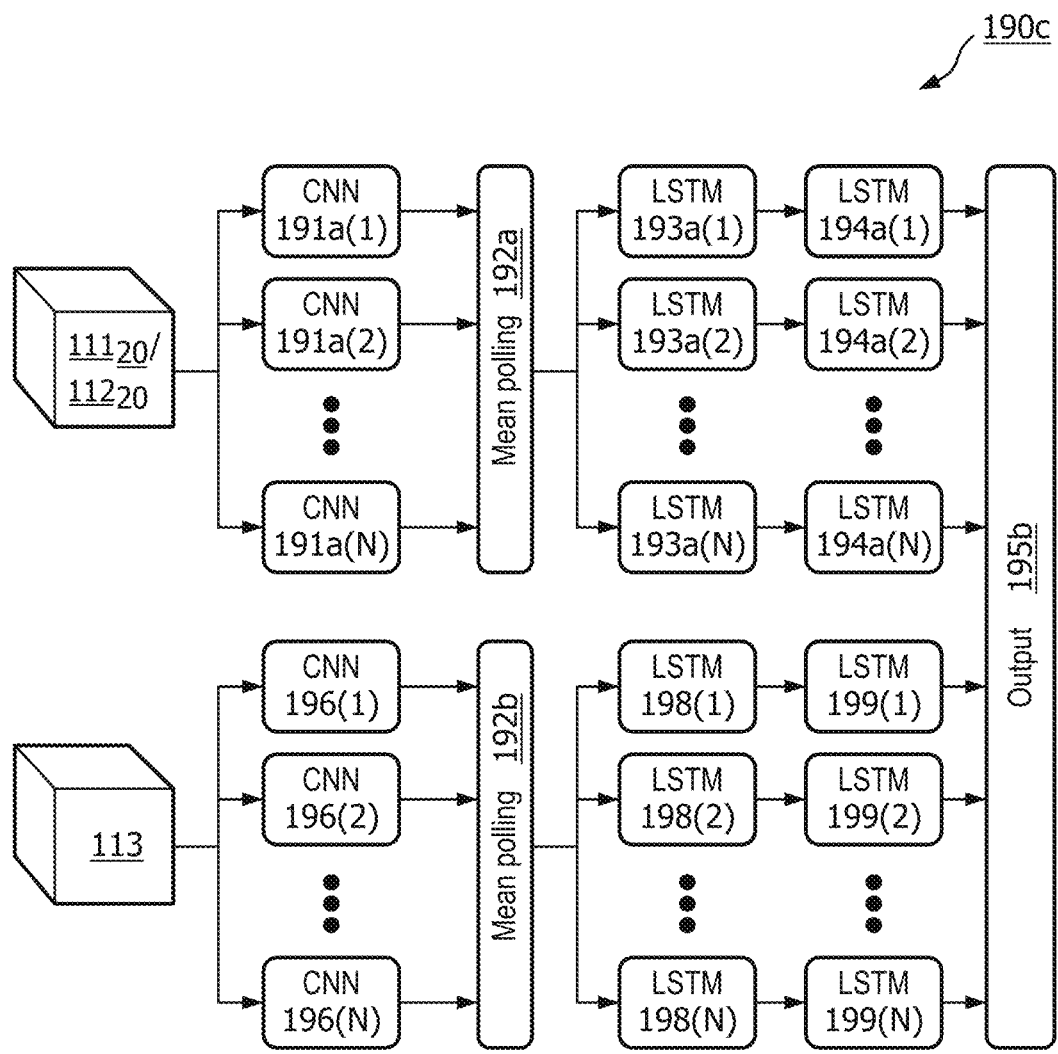
FIG. 5I illustrates an exemplary memory recurrent based convolutional neural analysis of an echocardiogram training volume and an electrocardiogram training volume in accordance with the principles of the present disclosure.

By further example, FIG. 5I illustrates a memory recurrent CNN 190c involving an execution of a mean polling 197 of a spatial-temporal CNN 196 for each electrocardiac wave of an electrocardiogram training volume 113, followed by an execution of a Long Short Term Memory (LSTM) RNN 198 and LSTM RNN 199 to obtain a scoring output 195c. In practice, a particular setup of training CNN 190c in terms of a complexity of spatial-temporal CNNs 191a and 196, and LSTM RNNs 193a, 193b, 198 and 199 will be dependent (1) a size of volumes 111/113 or of volumes 112/113 (whichever is being processed), (2) a desired detection accuracy of CNN 190c and (3) a type of abnormality that CNN 190c is designed to classify/quantify.

Referring back to FIG. 2A, normal echocardiogram classifier(s) 121 and abnormal echocardiogram classifier(s) 122 as generated by training convolution neural network 120 are utilized by a diagnostic convolution neural network for a real-time detection and characterization of any abnormality of a cardiac wall motion as will be further described in the present disclosure.

In practice, controller 100 may be installed in a workstation, accessible over a network by a workstation or distributed across a network.

Figure 6A:
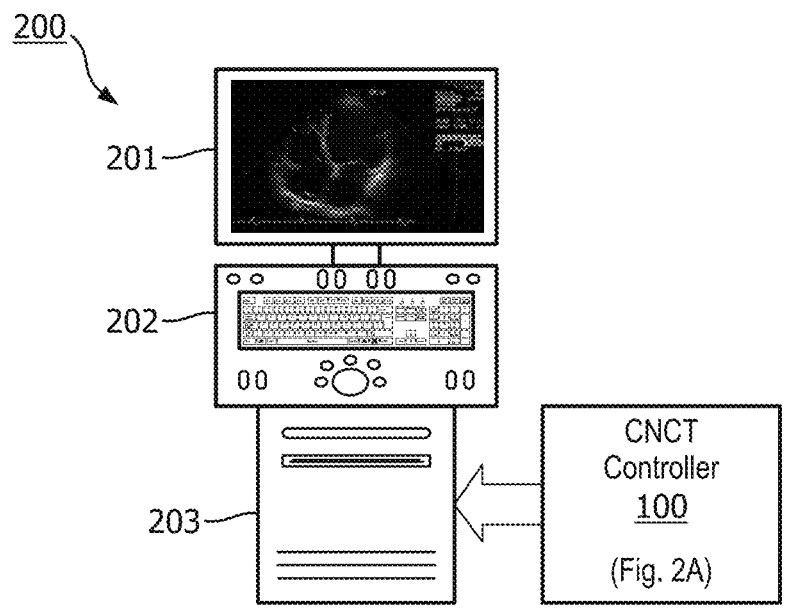
FIG. 6A illustrates a first exemplary embodiment of a convolutional neural cardiac training workstation in accordance with the principles of the present disclosure.

For example, FIG. 6A illustrates a workstation 200 employing a monitor 201, an input device 202 and a computer 203 having controller 100 installed therein.

Figure 6B:
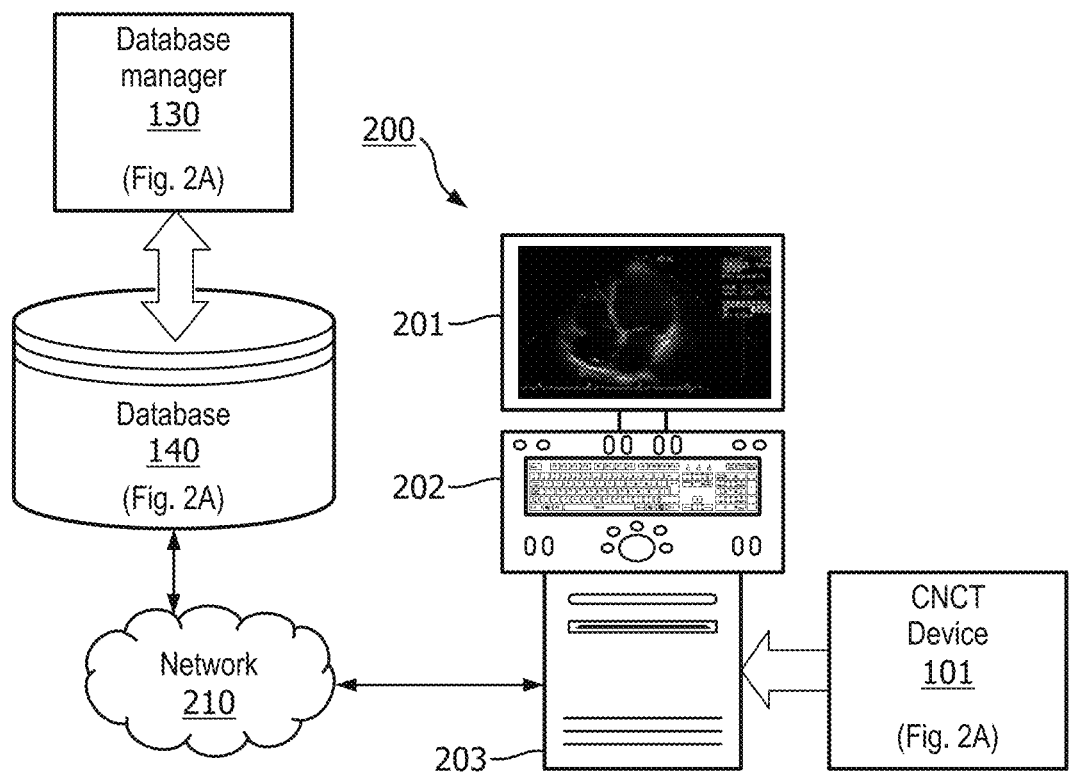
FIG. 6B illustrates a second exemplary embodiment of a convolutional neural cardiac training workstation in accordance with the principles of the present disclosure.

By further example, FIG. 6B illustrates a workstation 200 employing a monitor 201, an input device 202 and a computer 203 having a convolutional neural cardiac training device 101 installed therein. Device 101 employs training periodic volume generator 110 (FIG. 2A) and training CNN 120 (FIG. 2A) whereby database 140 (FIG. 2A) as managed by database manager 130 is accessible by periodic volume generator 110 via a network 210 of any type known in the art of the present disclosure.

Also in practice, controller 100 and device 101 may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface.

The network interface may include one or more devices, as known in the art of the present disclosure or hereinafter conceived, for enabling communication with other hardware devices. In an non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent\

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage may further store one or more application modules in the form of executable software/ firmware. Particularly, the storage stores executable software/firmware for training periodic volume generator 110 and training CNN 120.

To facilitate an understanding of a convolutional neural cardiac diagnostic aspect of the embodiments of the present disclosure, the following description of FIGS. 7-9B teaches general principles of an convolutional neural cardiac diagnostic aspect of the present disclosure. From this description, those having ordinary skill in the art will appreciate how to apply the general principles of the present disclosure for implementing numerous and various embodiments of convolutional neural cardiac diagnostics of the present disclosure.

Figure 7:
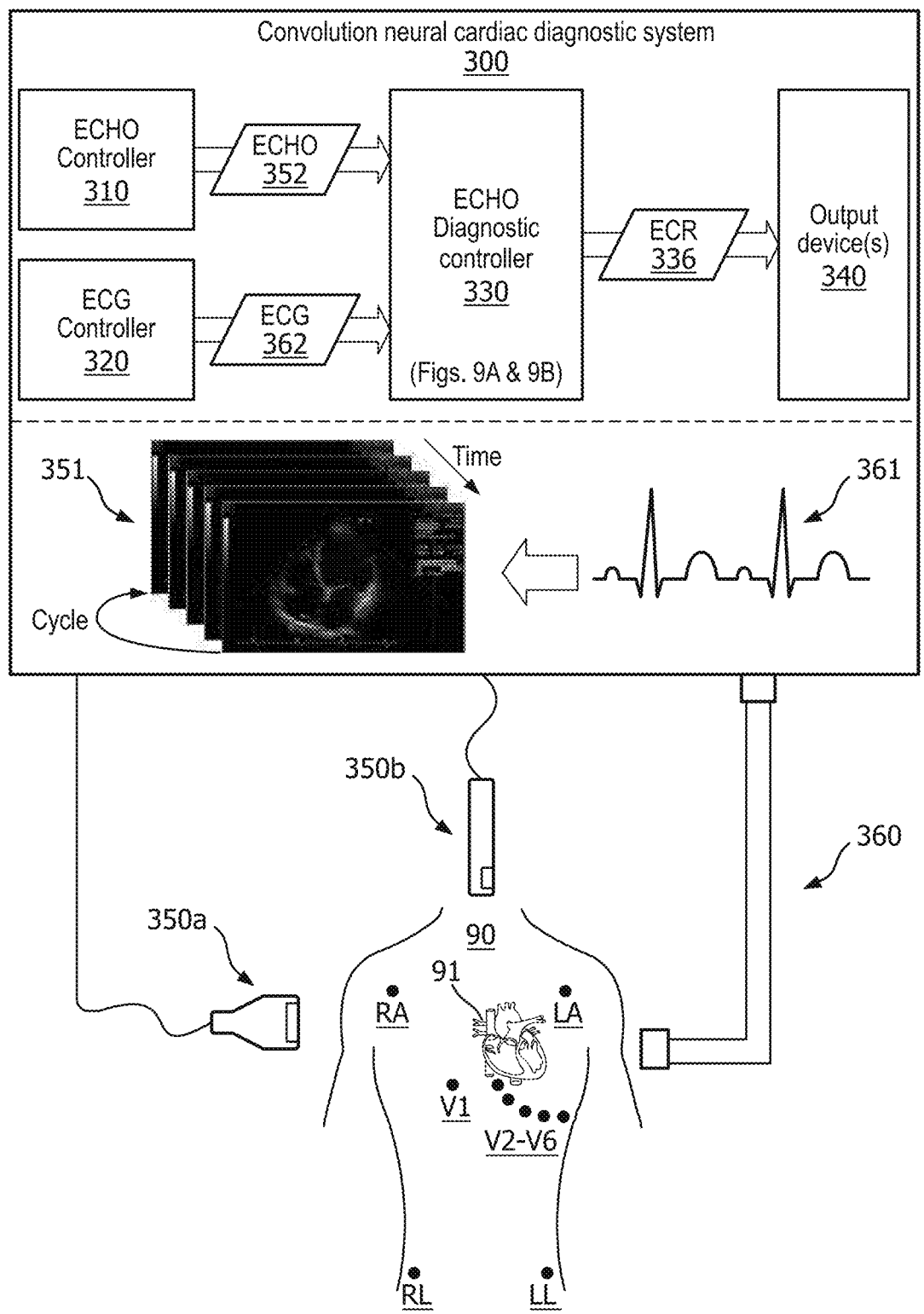
FIG. 7 illustrates an exemplary embodiment of a convolutional neural cardiac diagnostic system in accordance with the principles of the present disclosure.

Referring to FIG. 7, a convolutional neural cardiac diagnostic system 300 of the present disclosure employs an echocardiogram controller 310, a ECG wave controller 320, an echocardiogram diagnostic controller 330 and one or more output devices 340 (e.g., a display, a printer, a speaker and/or LED indicator(s)). In practice, controllers 310, 320 and 330 may be fully or partially integrated, or segregated as shown.

Echocardiogram controller 310 is linked to and/or incorporates any necessary hardware/software interface to an ultrasound transducer 350a or an ultrasound probe 350b positioned relative to a heart 91 of a patient 90 for receiving echocardiogram data to thereby generate an echocardiogram as known in the art of the present disclosure. The echocardiogram includes a temporal sequence of echocardiac cycles 351 with echocardiac cycle 351 includes a temporal sequence of 2D echo slices as shown or a 3D echo image. Echocardiogram controller 130 sequentially communicates a temporal sequence of echocardiac cycles 352 of echocardiogram 351 via wired and/or wireless channel(s) to echocardiogram diagnostic controller 330 as shown and to output device(s) 340 for display.

ECG controller 320 is linked to and/or incorporates any necessary hardware/software interface to a cable connector 360 for receiving electrode signals from a lead system connected to patient 90 (e.g., a standard 12-lead system, Mason-Likar lead system as shown or a reduced lead system like the EASI lead system) to thereby generate an electrocardiogram waveform 361 as known in the art of the present disclosure. Electrocardiogram waveform 361 includes a temporal sequence of ECG waves 362 as shown. Echocardiogram controller 130 sequentially communicates each ECG wave 362 of ECG waveform 361 via wired and/or wireless channel(s) to echocardiogram diagnostic controller 330 as shown and to output device(s) 340 for display.

Echocardiogram diagnostic controller 330 implement principles of the present disclosure for the detection and classification(quantification) of any abnormality of cardiac wall motion of heart 91 and for generating an echocardiogram classification report 336 indicating a normal or an abnormal cardiac wall motion of heart 91. In practice report 336, may be displayed or printed with textual and/or graphical information by output device(s) 340.

Figure 8A:
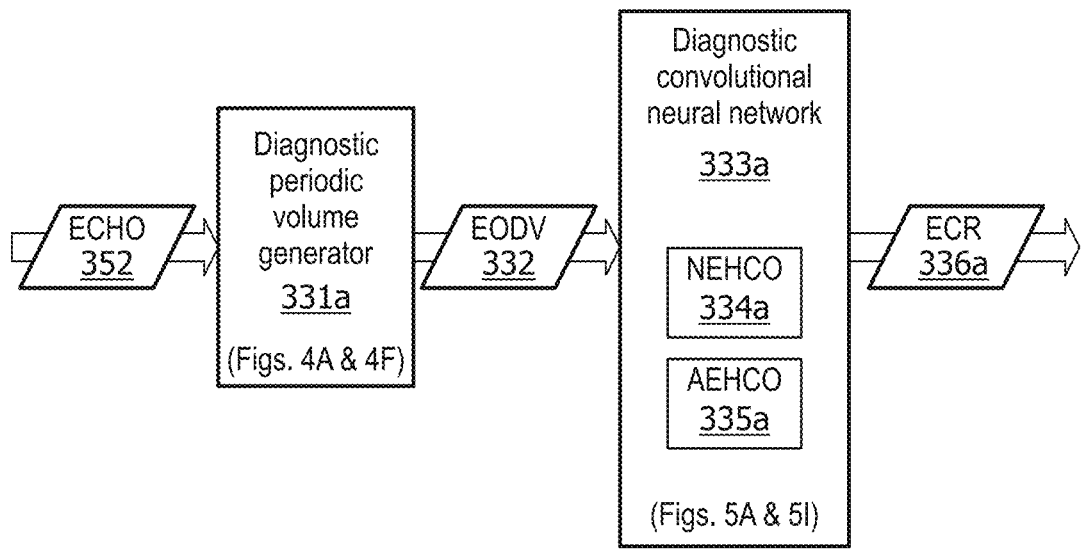
FIG. 8A illustrates a first exemplary embodiment of a convolutional neural cardiac diagnostic controller in accordance with the principles of the present disclosure.

In one embodiment, as shown in FIG. 8A, echocardiogram diagnostic controller 330 employs a diagnostic periodic volume generator 331a and a diagnostic convolutional neural network (CNN) 333a.

Periodic volume generator 331a is an application module structurally configured for processing echo cardio cycles 352 to generate an echocardiogram training volume 332 in accordance with the principles of the present disclosure previously described for training periodic volume generator 110 (FIG. 2A). In practice, echocardiogram training volume 332 consists of an X number of echo cardiac cycles 352, whereby X may be unlimited or have a maximum limitation of echo cardiac cycles 352 involving a first in, first out implementation of echo cardiac cycles 352.

The normality or the abnormality of echocardiogram training volume 332 is unknown.

Diagnostic CNN 333a therefore is an application module structurally configured for processing echocardiogram training volume 332 to generate an echocardiogram classification report 336a informative/illustrative of a normality or an abnormality of the cardiac wall motion of heart 91. More particularly, diagnostic CNN 333a executes a CNN whereby an output of the CNN is compared to a training normal echocardiogram classifier 334a and an abnormal training echocardiogram classifier 335a to detect and classify(quantify) a normality or an abnormality of the cardiac wall motion of heart 91.

In practice, diagnostic CNN 333a may execute any type of CNN known in the art of the present disclosure for delineating a connectivity pattern between motion features of echocardiogram training volume 332 that facilitates a classification of motion echocardiogram training volume 332. For example, diagnostic CNN 333a may execute a spatial-temporal CNN, a multiple stream CNN and/or a memory recurrent CNN as previously described in the present disclosure for training CNN 120 (FIGS. 5A-5I.

Also in practice, diagnostic CNN 333a may implement any technique as known in the art for use the CNN outputs to train diagnostic models based on a normal echocardiogram 334a and an abnormal echocardiogram 335a. For example, diagnostic CNN 333a may employ a neural network, SVM networks developed/trained from outputs of CNN for normal echocardiogram classifier 334a and an abnormal training echocardiogram classifier 335a

Figure 8B:
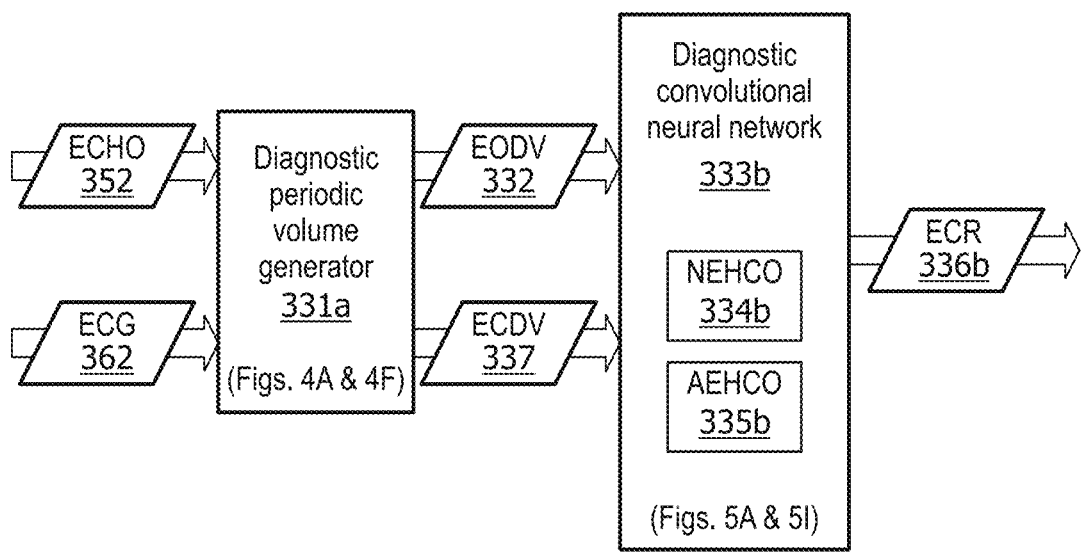
FIG. 8B illustrates a second exemplary embodiment of a convolutional neural cardiac diagnostic controller in accordance with the principles of the present disclosure.

In a second embodiment, as shown in FIG. 8b, echocardiogram diagnostic controller 330 employs a diagnostic periodic volume generator 331b and a diagnostic convolutional neural network (CNN) 333b.

Periodic volume generator 331b is an application module structurally configured for additionally processing ECG waves 362 to generate an electrocardiogram training volume 337 in accordance with the principles of the present disclosure previously described for training periodic volume generator 110 (FIG. 2A). In practice, electrocardiogram training volume 337 consists of an X number of ECG waves 362, whereby X may be unlimited or have a maximum limitation of ECG waves 362 involving a first in, first out implementation of ECG waves 362.

The normality or the abnormality of echocardiogram training volume 332 is unknown.

Diagnostic CNN 333b therefore is an application module structurally configured for processing both echocardiogram training volume 332 and electrocardiogram training volume 337 to generate an echocardiogram classification report 336b informative/illustrative of a normality or an abnormality of the cardiac wall motion of heart 91. More particularly, diagnostic CNN 333b executes a CNN whereby an output of the CNN is compared to a training normal echocardiogram classifier 334b and an abnormal training echocardiogram classifier 335b to detect and classify(quantify) a normality or an abnormality of the cardiac wall motion of heart 91.

In practice, diagnostic CNN 333a may execute any type of CNN known in the art of the present disclosure for delineating a connectivity pattern between motion features of echocardiogram training volume 332 and wave features of electrocardiogram training volume 337 that facilitates a classification of motion echocardiogram training volume 332. For example, diagnostic CNN 333b may execute a spatial-temporal CNN, a multiple stream CNN and/or a memory recurrent CNN as previously described in the present disclosure for training CNN 120 (FIGS. 5A-5I).

Also in practice, diagnostic CNN 333a may implement any technique as known in the art for use the CNN outputs to train diagnostic models based on a normal echocardiogram 334a and an abnormal echocardiogram 335a. For example, diagnostic CNN 333a may employ a neural network, SVM networks developed/trained from outputs of CNN for normal echocardiogram classifier 334a and an abnormal training echocardiogram classifier 335a Referring back to FIG. 7, in practice, echocardiogram controller 310, ECG controller 320 and echocardiogram diagnostic controller 330 may be installed in a workstation, accessible over a network by a workstation or distributed across a network.

Figure 9A:
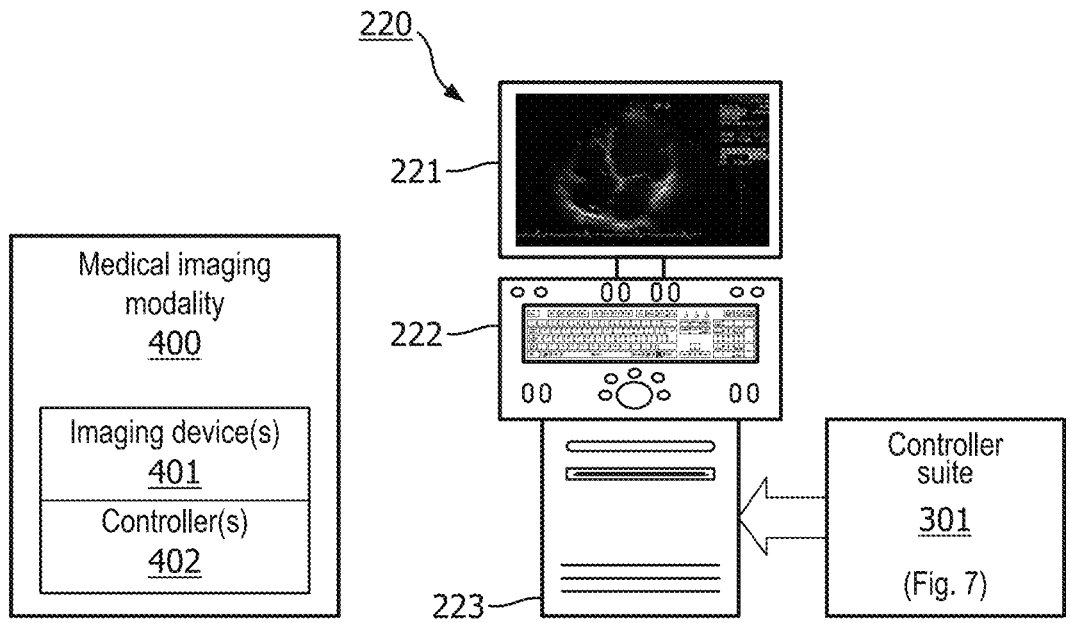
FIG. 9A illustrates an exemplary embodiment of a convolutional neural cardiac diagnostic workstation in accordance with the principles of the present disclosure.

For example, FIG. 9A illustrates a workstation 220 employing a monitor 221, an input device 222 and a computer 223 having controller suite 301 installed therein. Controller suite 301 includes controllers 310, 320 and 330.

Figure 9B:
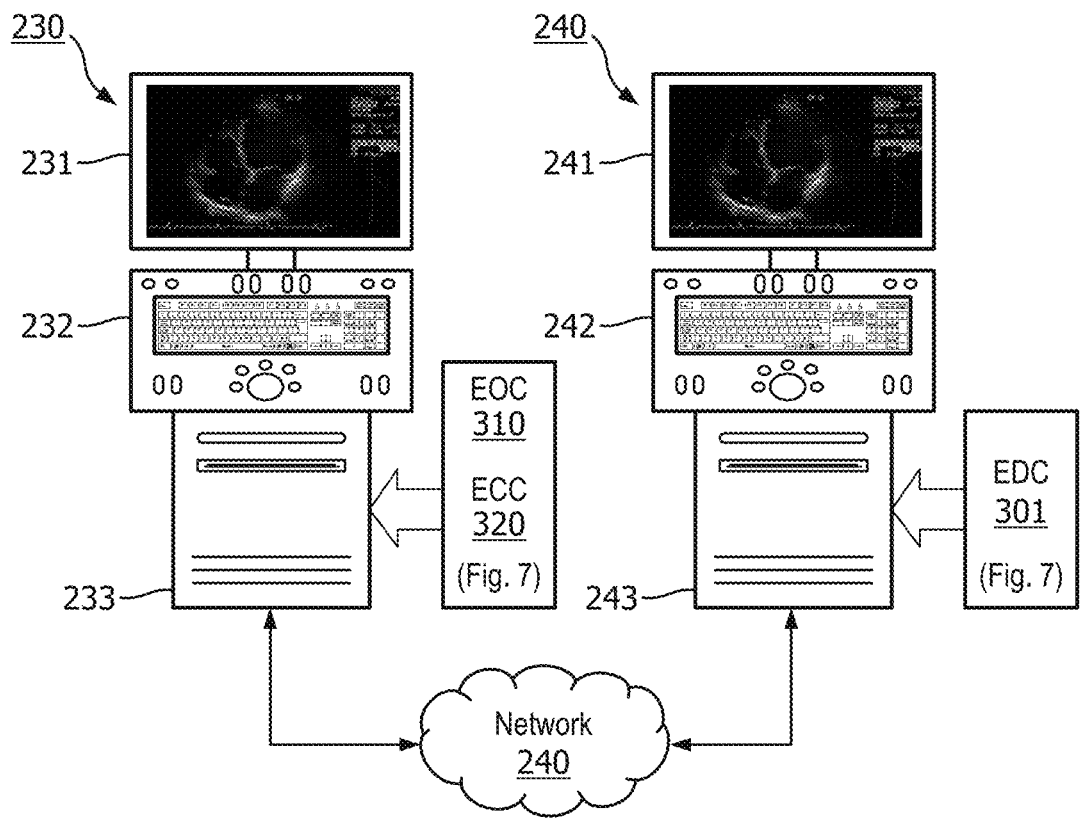
FIG. 9B illustrates an exemplary embodiment of a network pair of convolutional neural cardiac diagnostic workstations in accordance with the principles of the present disclosure.

By further example, FIG. 9B illustrates a workstation 230 employing a monitor 231, an input device 232 and a computer 233 having echocardiogram controller 310 and 320 installed therein, and further illustrates a workstation 240 employing a monitor 241, an input device 242 and a computer 243 having echocardiogram diagnostic controller 330 installed therein. Controllers 310, 320 and 330 communicate over a network 240 of any type as known in the art of the present disclosure.

Also in practice, controllers 310, 320 and 330 may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface.

The network interface may include one or more devices, as known in the art of the present disclosure or hereinafter conceived, for enabling communication with other hardware devices. In an non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent\

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage may further store one or more application modules in the form of executable software/firmware. Particularly, for echocardiogram diagnostic controller 330, the storage stores executable software/firmware for training periodic volume generator 331 and training CNN 333.

As previously described in the present disclosure, the principles of the present disclosure are applicable to any type of cardiac diagnostic procedure including, but not limited to, echocardiography, CT heart scans and cardiac MRI echocardiography, cardiac CT, cardiac MRI, angiography, cardiac positron emission tomography (PET) and cardiac single photon computed emission tomography (SPECT). Thus, while the embodiments of the present disclosure were described in the context of an echocardiography application, FIG. 9A illustrates a medical imaging modality 400 representative of an application of any type of cardiac diagnostic procedure for detecting and classifying (quantifying) a normality or an abnormality of a cardiogram applicable to the particular cardiac diagnostic procedure.

Specifically, examples of medical imaging modality 400 includes, but are not limited to, an ultrasound imaging modality, a X-ray computed tomography imaging modality, a magnetic resonance imaging modality, a fluoroscopic imaging modality, a position emission tomography imaging modality and a single-photo emission computed tomography imaging modality. Any embodiment of medical imaging modality 400 employs applicable imaging device(s) 401 and controller(s) 402 for generating cardiograms as known in the art of the present disclosure. Thus, the training and diagnostic aspects of the present disclosure are based on the particular type of cardiac imaging. In practice, the particular type of cardiac imaging may generate 2D planar and 3D volume images as exemplary shown herein and/or generate high dimensional imaging as known in the art of the present disclosure.

Referring to FIGS. 1-9, those having ordinary skill in the art will appreciate numerous benefits of the present disclosure including, but not limited to, (1) a reduction of intra-observer and inter-observer variability in interpreting echo image, (2) an allowance for a robot real-time diagnosis of a cardiovascular disease, (3) an improvement in reader confidence and a reduction in reading time of echo image and (4) an improvement in an accuracy of cardiovascular disease diagnosis by combining information contained in echo image with electrocardiogram waves.

Furthermore, as one having ordinary skill in the art will appreciate in view of the teachings provided herein, features, elements, components, etc. described in the present disclosure/specification and/or depicted in the drawings of the present disclosure may be implemented in various combinations of electronic components/circuitry, hardware, executable software and executable firmware, particularly as application modules of a controller as described in the present disclosure, and provide functions which may be combined in a single element or multiple elements. For example, the functions of the various features, elements, components, etc. shown/illustrated/depicted in the drawings of the present disclosure can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles described herein. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk—read only memory (CD-ROM), compact disk—read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described example embodiments of various systems, controllers and methods for convolutional deep learning analysis of temporal diagnostic echo images, (which embodiments are intended to be illustrative and not limiting), it is noted that modifications and variations can be made by persons having ordinary skill in the art in light of the teachings provided herein, including the drawings of the present disclosure. It is therefore to be understood that changes can be made in/to the example embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A convolutional neural cardiac diagnostic system, comprising:
    an echocardiogram diagnostic controller structurally configured to control a diagnosis of an echocardiogram including a temporal sequence of echocardiac cycles, wherein the echocardiogram diagnostic controller includes:
        a diagnostic periodic volume generator structurally configured to generate an echocardiogram diagnostic volume derived from the echocardiogram, the echocardiogram diagnostic volume including a periodic stacking of the temporal sequence of echocardiac cycles; and
        a diagnostic convolutional neural network structurally configured to classify the echocardiogram as one of a normal echocardiogram or an abnormal echocardiogram based on a convolutional neural analysis of the echocardiogram diagnostic volume as generated by the diagnostic periodic volume generator.

2. The convolutional neural cardiac diagnostic system of claim 1, further comprising:
    an ultrasound device structurally configured to generate echocardiogram data; and
    an echocardiogram controller structurally configured to control a generation of the echocardiogram derived from a generation of the echocardiogram data by the ultrasound device, the echocardiogram including a temporal sequence of echocardiac cycles.

3. The convolutional neural cardiac diagnostic system of claim 1, wherein the temporal sequence of echocardiac cycles include one of:
    planar echocardiac images; and
    volumetric echocardiac images.

4. The convolutional neural cardiac diagnostic system of claim 1,
    wherein the echocardiogram includes an additional temporal sequence of echocardiac cycles;
    wherein the diagnostic periodic volume generator is further structurally configured to generate an additional echocardiogram diagnostic volume including an periodic stacking of the additional temporal sequence of echocardiac cycles; and
    wherein the diagnostic convolutional neural network is further structurally configured to classify the echocardiogram as one of a normal echocardiogram or an abnormal echocardiogram based on a convolutional neural analysis of both the echocardiogram diagnostic volume and the additional echocardiogram diagnostic volume as generated by the diagnostic periodic volume generator.

5. The convolutional neural cardiac diagnostic system of claim 1, wherein the diagnostic convolutional neural network includes at least one of a spatial-temporal based convolutional neural network, a multiple stream based convolutional neural network, and a memory recurrent network based convolutional neural network.

6. The convolutional neural cardiac diagnostic system of claim 1,
wherein the diagnostic periodic volume generator is further structurally configured to generate an electrocardiogram diagnostic volume derived from an electrocardiogram the temporal sequence of electrocardiac waves, the electrocardiogram diagnostic volume including a periodic stacking of the temporal sequence of electrocardiac waves; and
wherein the diagnostic convolutional neural network is structurally configured to classify the echocardiogram as one of the normal echocardiogram or the abnormal echocardiogram based on a convolutional neural analysis of both the echocardiogram diagnostic volume and the electrocardiogram diagnostic volume as generated by the diagnostic periodic volume generator.

7. The convolutional neural cardiac diagnostic system of claim 6, further comprising:
a lead system structurally configured to generate electrocardiogram data; and
an electrocardiogram controller structurally configured to control a generation of the electrocardiogram derived from a generation of the electrocardiogram data by the lead system.

8. A convolutional neural cardiac diagnostic system, comprising:
a cardiogram diagnostic controller structurally configured to control a diagnosis of a cardiogram including a temporal sequence of cardiac cycles, wherein the cardiogram diagnostic controller includes:
a diagnostic periodic volume generator structurally configured to generate a cardiogram diagnostic volume derived from a generation of the cardiogram by the cardiogram controller, the cardiogram diagnostic volume including a periodic stacking of the temporal sequence of cardiac cycles; and
a diagnostic convolutional neural network structurally configured to classify the cardiogram as one of a normal cardiogram or an abnormal cardiogram based on a convolutional neural analysis of the cardiogram diagnostic volume as generated by the diagnostic periodic volume generator.

9. The convolutional neural cardiac diagnostic system of claim 8, further comprising:
a medical imaging modality structurally configured to generate cardiac imaging data; and
a cardiogram controller structurally configured to control a generation of the cardiogram derived from a generation of the cardiac imaging data by the imaging modality.

10. The convolutional neural cardiac diagnostic system of claim 9,
wherein the medical imaging modality includes at least one of an ultrasound imaging device, a X-ray computed tomography imaging device, a magnetic resonance imaging device, a fluoroscopic imaging device, a position emission tomography imaging device and a single-photo emission computed tomography imaging device.

11. The convolutional neural cardiac diagnostic system of claim 8, wherein the temporal sequence of cardiac cycles are one of:
planar cardiac images;
volumetric cardiac images; and
high dimensional cardiac images.

12. The convolutional neural cardiac diagnostic system of claim 8,
wherein the cardiogram includes an additional temporal sequence of cardiac cycles;
wherein the diagnostic periodic volume generator is further structurally configured to generate an additional cardiogram diagnostic volume including an periodic stacking of the additional temporal sequence of cardiac cycles; and
wherein the diagnostic convolutional neural network is further structurally configured to classify the cardiogram as one of a normal cardiogram or an abnormal cardiogram based on a convolutional neural analysis of both the cardiogram diagnostic volume and the additional cardiogram diagnostic volume as generated by the diagnostic periodic volume generator.

13. The convolutional neural cardiac diagnostic system of claim 8,
wherein the diagnostic convolutional neural network includes at least one of a spatial-temporal based convolutional neural network, a multiple stream based convolutional neural network, and a memory recurrent network based convolutional neural network.

14. The convolutional neural cardiac diagnostic system of claim 8,
wherein the diagnostic periodic volume generator is further structurally configured to generate an electrocardiogram diagnostic volume derived from an electrocardiogram including a temporal sequence of electrocardiac waves, the electrocardiogram diagnostic volume including a periodic stacking of the temporal sequence of electrocardiac waves; and
wherein the diagnostic convolutional neural network is structurally configured to classify the cardiogram as one of the normal cardiogram or the abnormal cardiogram based on a convolutional neural analysis of both the cardiogram diagnostic volume and the electrocardiogram diagnostic volume as generated by the diagnostic periodic volume generator.

15. The convolutional neural cardiac diagnostic system of claim 8, further comprising:
a lead system structurally configured to generate electrocardiogram data; and
an electrocardiogram controller structurally configured to control a generation of the electrocardiogram derived from a generation of the electrocardiogram data by the lead system.

16. A convolutional neural cardiac diagnostic method, comprising:
an echocardiogram diagnostic controller controlling a diagnosis of an echocardiogram temporal sequence of echocardiac cycles, the diagnosis including:
the echocardiogram diagnostic controller generating an echocardiogram diagnostic volume derived from the echocardiogram, the echocardiogram diagnostic volume including a periodic stacking of the temporal sequence of echocardiac cycles; and
the echocardiogram diagnostic controller classifying the echocardiogram as one of a normal echocardiogram or an abnormal echocardiogram based on a convolutional neural analysis of the echocardiogram diagnostic volume.

17. The convolutional neural cardiac diagnostic method of claim 16, wherein the echocardiogram includes an additional temporal sequence of echocardiac cycles;

wherein the echocardiogram diagnostic controller further generates an additional echocardiogram diagnostic volume including an periodic stacking of the additional temporal sequence of echocardiac cycles; and wherein the echocardiogram diagnostic controller classifies the echocardiogram as one of a normal echocardiogram or an abnormal echocardiogram based on a convolutional neural analysis of both the echocardiogram diagnostic volume and the additional echocardiogram diagnostic volume.

18. The convolutional neural cardiac diagnostic method of claim 16, further comprising:

an ultrasound device generating echocardiogram data; and an echocardiogram controller controlling a generation of the echocardiogram derived from the generation of the echocardiogram data by the ultrasound device.

19. The convolutional neural cardiac diagnostic method of claim 16, further comprising:

the diagnosis including:

the echocardiogram diagnostic controller generating an electrocardiogram diagnostic volume derived from an electrocardiogram including a temporal sequence of electrocardiac waves, the electrocardiogram diagnostic volume including a periodic stacking of the temporal sequence of electrocardiac waves; and the echocardiogram diagnostic controller classifying the echocardiogram as one of the normal echocardiogram or the abnormal echocardiogram responsive to a convolutional analysis of both the echocardiogram diagnostic volume and the electrocardiogram diagnostic volume.

20. The convolutional neural cardiac diagnostic method of claim 19, further comprising:

a lead system generating electrocardiogram data; and an electrocardiogram controller controlling a generation of the electrocardiogram derived from a generation of the electrocardiogram data by the lead system.

* * * * *